US012778419B2

(12) United States Patent
Ohara et al.

(10) Patent No.: US 12,778,419 B2
(45) Date of Patent: Nov. 3, 2026

(54) OPHTHALMIC INFORMATION PROCESSING APPARATUS, OPHTHALMIC APPARATUS, OPHTHALMIC INFORMATION PROCESSING METHOD, AND RECORDING MEDIUM

(71) Applicant: Topcon Corporation, Tokyo (JP)

(72) Inventors: Ryuichi Ohara, Tokyo (JP); Jun Sakai, Kuki (JP); Hiroyuki Aoki, Saitama (JP)

(73) Assignee: TOPCON CORPORATION, Tokyo (JP)

( * ) Notice: Subject to any disclaimer, the term of this patent is extended or adjusted under 35 U.S.C. 154(b) by 561 days.

(21) Appl. No.: 18/106,494

(22) Filed: Feb. 7, 2023

(65) Prior Publication Data

US 2023/0389795 A1 Dec. 7, 2023

(30) Foreign Application Priority Data

Jun. 3, 2022 (JP) ................................ 2022-091120

(51) Int. Cl.

*A61B 3/00* (2006.01)
*A61B 3/14* (2006.01)
*A61B 3/10* (2006.01)

(52) U.S. Cl.

CPC .............. *A61B 3/14* (2013.01); *A61B 3/0025* (2013.01); *A61B 3/102* (2013.01)

(58) Field of Classification Search

CPC ......... A61B 3/14; A61B 3/0025; A61B 3/102; A61B 3/0008; A61B 3/028; A61B 3/13

See application file for complete search history.

(56) References Cited

U.S. PATENT DOCUMENTS

| | | | | |
|---|---|---|---|---|
| 6,728,401 | B1 * | 4/2004 | Hardeberg ............. | H04N 1/624 348/576 |
| 7,831,106 | B2 | 11/2010 | Elsner et al. | |
| 8,237,835 | B1 | 8/2012 | Muller | |
| 11,885,959 | B1 * | 1/2024 | Hsu ...................... | G02B 27/286 |
| 2003/0231242 | A1 | 12/2003 | Matsumoto | |

(Continued)

FOREIGN PATENT DOCUMENTS

| | | | |
|---|---|---|---|
| JP | 61-293430 | A | 12/1986 |
| JP | 2004016486 | A | 1/2004 |

(Continued)

OTHER PUBLICATIONS

Office Action issued Dec. 9, 2025, in corresponding Japanese Patent Application No. 2022-091120, 6pp.

*Primary Examiner* — Bumsuk Won
*Assistant Examiner* — John C Sipes
(74) *Attorney, Agent, or Firm* — XSENSUS LLP

(57) ABSTRACT

An ophthalmic information processing apparatus is configured to remove an artifact of an image of a subject's eye obtained using an ophthalmic apparatus. The ophthalmic information processing apparatus includes an identifying unit and a correction unit. The identifying unit is configured to identify a correction region in the image based on a dioptric power of the subject's eye. The correction unit is configured to correct a luminance in the correction region identified by the identifying unit, based on a correction amount corresponding to the dioptric power of the subject's eye.

14 Claims, 19 Drawing Sheets

(56) References Cited

U.S. PATENT DOCUMENTS

| | | | | |
|---|---|---|---|---|
| 2008/0123050 | A1* | 5/2008 | Tanaka | A61B 3/14 351/206 |
| 2008/0253622 | A1* | 10/2008 | Tosa | G06T 7/149 382/117 |
| 2014/0340635 | A1* | 11/2014 | Oyaizu | A61B 3/0091 351/212 |
| 2015/0085252 | A1 | 3/2015 | Fujimura et al. | |
| 2016/0345822 | A1 | 12/2016 | Fujimura et al. | |
| 2018/0064338 | A1* | 3/2018 | Neal | A61B 3/107 |
| 2019/0370942 | A1* | 12/2019 | Gatt | G06T 7/187 |
| 2021/0224997 | A1* | 7/2021 | Kushida | G06T 7/12 |
| 2021/0290050 | A1 | 9/2021 | Shiba et al. | |
| 2021/0311286 | A1* | 10/2021 | Lee | G02B 27/14 |
| 2023/0396883 | A1* | 12/2023 | Kamal | H04N 23/81 |
| 2024/0252036 | A1* | 8/2024 | Lussier | G02B 27/0075 |

FOREIGN PATENT DOCUMENTS

| | | | |
|---|---|---|---|
| JP | 2007185417 | A | 7/2007 |
| JP | 2010-259495 | A | 11/2010 |
| JP | 2013-248376 | A | 12/2013 |
| JP | 2017-42312 | A | 3/2017 |
| JP | 2021-104229 | A | 7/2021 |
| JP | 2022077565 | A | 5/2022 |

* cited by examiner

OPHTHALMIC INFORMATION PROCESSING APPARATUS, OPHTHALMIC APPARATUS, OPHTHALMIC INFORMATION PROCESSING METHOD, AND RECORDING MEDIUM

CROSS-REFERENCE TO RELATED APPLICATION

This application is based upon and claims the benefit of priority from Japanese Patent Application No. 2022-091120, filed Jun. 3, 2022, the entire contents of which are incorporated herein by reference.

FIELD

The disclosure relates to an ophthalmic information processing apparatus, an ophthalmic apparatus, an ophthalmic information processing method, and a recording medium.

BACKGROUND

Images of a subject's eye acquired using ophthalmic apparatuses such as ophthalmic imaging apparatuses are useful for diagnosis of eyes. Ophthalmic information processing apparatuses can generate information to assist in diagnosing the eyes by analyzing the acquired images of the eyes of the subjects. Thereby, the accuracy of diagnosing eyes can be improved.

For example, U.S. Pat. Nos. 7,831,106, 8,237,835, and Japanese Unexamined Patent Application Publication No. 2021-104229 disclose ophthalmic apparatuses configured to acquire fundus images by pattern-illuminating the subject's eye using slit-shaped light and detecting returning light thereof using image sensor. These ophthalmic apparatuses can acquire images of the subject's eye with a simple configuration, by adjusting the illumination pattern and the timing of light receiving using the image sensor.

It is known that apparatus-derived artifacts such as the optical elements included in the optical system provided in the ophthalmic apparatus and the arrangement of the optical system are depicted in images acquired using such ophthalmic apparatuses. For example, Japanese Unexamined Patent Application Publication No. 2021-104229 discloses a method of acquiring an image for correction in which artifacts alone caused by reflection light of illumination light by an objective lens, etc. are depicted, acquiring a plurality of conversion images by performing a plurality of conversion processing on the image for correction while changing the processing contents, searching for a difference image in which the effect of artifacts is suppressed to a standard or lower among a plurality of difference images between each of the plurality of conversion images and a fundus image, and acquiring the searched difference image as a high quality image.

SUMMARY

One aspect of embodiments is an ophthalmic information processing apparatus for removing an artifact of an image of a subject's eye obtained using an ophthalmic apparatus. The ophthalmic information processing apparatus includes: an identifying unit configured to identify a correction region in the image based on a dioptric power of the subject's eye; and a correction unit configured to correct a luminance in the correction region identified by the identifying unit, based on a correction amount corresponding to the dioptric power of the subject's eye.

Another aspect of the embodiments is an ophthalmic apparatus including: an illumination optical system configured to irradiate illumination light onto the subject's eye; an imaging optical system configured to acquire an image of the subject's eye by receiving returning of the illumination light from the subject's eye; and the ophthalmic information processing apparatus, described above, configured to remove an artifact of the image acquired by the imaging optical system.

Still another aspect of the embodiments is an ophthalmic information processing method of removing an artifact of an image of a subject's eye obtained using an ophthalmic apparatus. The ophthalmic information processing method includes: an identifying step of identifying a correction region in the image based on a dioptric power of the subject's eye; and a correction step of correcting a luminance in the correction region identified in the identifying step, based on a correction amount corresponding to the dioptric power of the subject's eye.

Still another aspect of the embodiments is a computer readable non-transitory recording medium in which a program for causing a computer to execute each step of the ophthalmic information processing method described above is recorded.

DETAILED DESCRIPTION

Figure 1A:
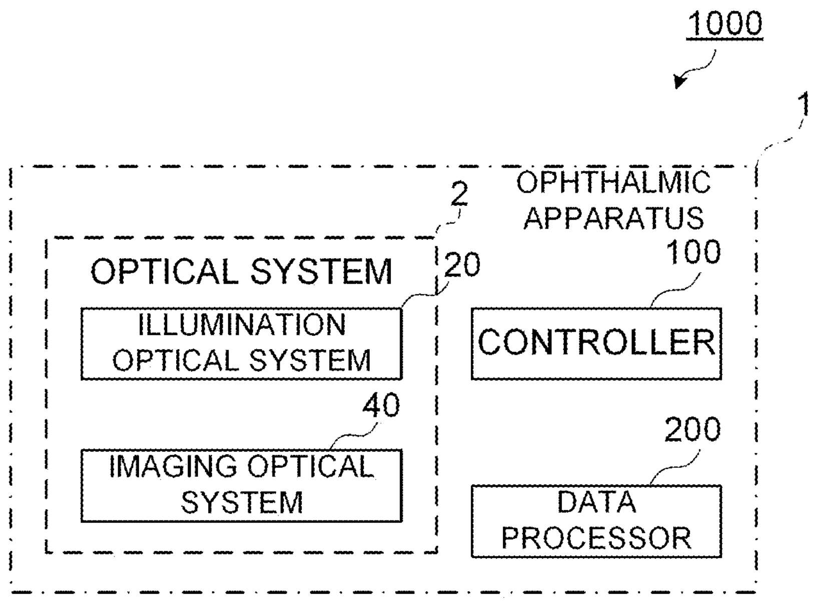
FIG. 1A is a schematic diagram illustrating a first configuration example of an ophthalmic system according to embodiments.

In the method disclosed in Japanese Unexamined Patent Application Publication No. 2021-104229, the image for correction must be acquired in advance. As a result, in addition to increasing the number of processes required to remove artifacts, the processing load for removing artifacts becomes heavy. Further, the accuracy of artifact removal depends on the state of the artifacts depicted in the image for correction, and the accuracy of artifact removal varies depending on the dioptric power of the subject's eye.

According to some embodiments of the present invention, a new technique for removing artifacts in the image of the subject's eye that vary in accordance with the dioptric power of the subject's eye with a simple processing can be provided.

Referring now to the drawings, exemplary embodiments of an ophthalmic information processing apparatus, an ophthalmic apparatus, an ophthalmic information processing method, a program, and a recording medium according to the present invention are described below. The contents of the document cited in the present specification can be appropriately incorporated as contents of the following embodiments.

In the following detailed description, for purposes of explanation, numerous specific details are set forth in order to provide a thorough understanding of the disclosed embodiments. It will be apparent, however, that one or more embodiments may be practiced without these specific details. In other instances, well-known structures and devices are schematically shown in order to simplify the drawing.

An ophthalmic information processing apparatus according to embodiments can identify a correction region in an image of the subject's eye based on a state of the subject's eye. Here, the correction region corresponds to a shape of an artifact that is depicted in the image and that varies in accordance with the state of the subject's eye. And the ophthalmic information processing apparatus can correct the identified correction region based on a correction amount corresponding to the state of the subject's eye.

Examples of the state of the subject's eye include a dioptric power (refractive power) of the subject's eye, a shape of a fundus of the subject's eye. Examples of the image of the subject's eye include a fundus image (front image), an anterior segment image, a posterior segment image, a tomographic image.

Examples of the artifact include an artifact derived from the ophthalmic apparatus that acquires the image of the subject's eye. The artifact derived from the ophthalmic apparatus means an artifact caused by an optical condition (arrangement of optical system, characteristics of optical element) in an optical system included in the ophthalmic apparatus. Examples of such artifact include a black dot shadow and a center ghost. The black dot shadow is a shadow that is reflected in the photographic image, the shadow being formed by a black dot (black dot plate), which is placed in the optical system so as to remove reflection ghost due to the reflection from the objective lens, by partially blocking the illumination light. The center ghost is a ghost or an artifact in which reflection light of the illumination light from near the optical axis of the objective lens is reflected in the photographic image. The black dot shadow changes in position, shape, and intensity (color and shade of the shadow) in accordance with the dioptric power of the subject's eye. The center ghost changes in position, shape, and intensity (color and brightness of flare) in accordance with the dioptric power of the subject's eye. Examples of the correction include a luminance correction for correcting the luminance value of a pixel.

This allows to remove the artifacts varying in accordance with the state of the subject's eye with high precision or to significantly suppress the effects of the artifacts, with a simple process.

In some embodiments, the ophthalmic information processing apparatus is configured to store artifact information for each dioptric power for identifying the position, the shape, and the intensity of the artifact(s) in the image, to identify the correction region in the image based on the artifact information corresponding to the dioptric power of the subject's eye, and to correct the correction region based on the artifact information. For example, the artifact information is calculated by performing an optical simulation in advance for each dioptric power, under a simulation condition corresponding to an optical condition in the optical system provided in the ophthalmic apparatus for acquiring images of the subject's eye. For example, the artifact information is acquired by measuring in advance for each dioptric power, using the ophthalmic apparatus for acquiring images of the subject's eye.

In some embodiments, an analysis region is identified. Here, the analysis region is a region shifted from a reference position in the image by a displacement of the reference position that varies in accordance with the dioptric power of the subject's eye, based on the dioptric power of the subject's eye and the optical condition in the optical system provided in the ophthalmic apparatus that acquires image of the subject's eye. Examples of the reference position in the image include a position corresponding to the optical axis of the optical system in the ophthalmic apparatus and a center position of the image. For example, the correction region is identified within the identified analysis region.

The ophthalmic information processing apparatus according to the embodiments acquires an image of the subject's eye from an ophthalmic apparatus having a function of an ophthalmic imaging apparatus, for example. Further, the ophthalmic information processing apparatus according to the embodiments can acquire the dioptric power of the subject's eye from the ophthalmic apparatus having a function of the ophthalmic imaging apparatus that can perform focus control, for example. In this case, the ophthalmic information processing apparatus acquires a focus control result in the ophthalmic apparatus or the dioptric power corresponding to the focus control result. Examples of the focus control result include a focusing position of a focusing lens obtained as the focus control result by the focusing lens that is movable in the optical axis direction. Alternatively, the ophthalmic information processing apparatus according to the embodiments may acquire the dioptric power of the subject's eye from an ophthalmic apparatus having a function of a refractive power measurement. In some embodiments, the ophthalmic apparatus has the function of the ophthalmic information processing apparatus according to the embodiments.

An ophthalmic information processing method according to the embodiments includes one or more steps for realizing the processing executed by a processor (computer) in the ophthalmic information processing apparatus according to the embodiments. A program according to the embodiments causes the processor to execute each step of the ophthalmic information processing method according to the embodiments. A recording medium (storage medium) according to the embodiments is a computer readable non-transitory recording medium (storage medium) on which the program according to the embodiments is recorded.

The term "processor" as used herein refers to a circuit such as, for example, a central processing unit (CPU), a graphics processing unit (GPU), an application specific integrated circuit (ASIC), and a programmable logic device (PLD). Examples of PLD include a simple programmable logic device (SPLD), a complex programmable logic device (CPLD), and a field programmable gate array (FPGA). The processor realizes, for example, the function according to the embodiments by reading out a computer program stored in a storage circuit or a storage device and executing the computer program.

In the following embodiments, a case will be mainly described where the artifact that varies in accordance with the dioptric power of the subject's eye is removed. However, the following embodiments can also be applied to the case where the artifacts that vary according to the state (condition) of the subject's eye other than the dioptric power is/are removed.

<Ophthalmic System>

An ophthalmic system according to the embodiments realizes (implements) at least the function of the ophthalmic information processing apparatus according to the embodiments. Further, the ophthalmic system can include one or more ophthalmic apparatuses that transmit images of the subject's eye and dioptric power information including the dioptric power of the subject's eye to the ophthalmic information processing apparatus via a predetermined communication means. The ophthalmic apparatus that transmits the image of the subject's eye to the ophthalmic information processing apparatus has an optical system similar to that of the ophthalmic imaging apparatus with the configuration disclosed in any one of U.S. Pat. Nos. 7,831,106, 8,237,835, and Japanese Unexamined Patent Application Publication No. 2021-104229, for example. The ophthalmic apparatus that transmits the dioptric power information to the ophthalmic information processing apparatus has an optical system similar to that of the ophthalmic imaging apparatus that can transmit the focus control result as the dioptric power information or the refractive power measurement apparatus having the configuration disclosed in Japanese Unexamined Patent Application No. 61-293430 or Japanese Unexamined Patent Application Publication No. 2010-259495, for example.

FIG. 1A shows a functional block diagram of a first configuration example of the ophthalmic system according to the embodiments.

The ophthalmic system 1000 according to the first configuration example includes an ophthalmic apparatus 1. The ophthalmic apparatus 1 realizes the functions of the ophthalmic information processing apparatus according to the embodiments and the functions of the ophthalmic imaging apparatus.

The ophthalmic apparatus 1 includes an optical system 2, a controller 100, and a data processor 200. The optical system 2 includes an optical system for acquiring images of the subject's eye. The controller 100 controls each part (optical system 2, data processor 200) of the ophthalmic apparatus 1. The functions of the controller 100 are realized by a processor, for example. The data processor 200 realizes the functions of the ophthalmic information processing apparatus according to the embodiments. In other words, the data processor 200 identifies the correction region in the image of the subject's eye based on the dioptric power of the subject's eye. Here, the correction region corresponds to the shape of the artifact(s) depicted in the image of the subject's eye. And then, the data processor 200 performs artifact removal processing for correcting the correction region with the correction amount corresponding to the dioptric power of the subject's eye. The functions of such data processor 200 are realized, for example, by a processor.

The optical system 2 includes an illumination optical system 20 and an imaging (photographing) optical system 40. The illumination optical system 20 illuminates the subject's eye with illumination light from a light source. In some embodiments, the illumination optical system 20 includes the light source. The imaging optical system 40 includes a focusing lens that is movable in the optical axis direction under the control from the controller 100. The imaging optical system 40 guides returning light of the illumination from the subject's eye to an imaging device. The controller 100 can identify the dioptric power of the subject's eye from the focus control result for the focusing lens. In some embodiments, the imaging optical system 40 includes the imaging device.

In such ophthalmic system 1000, under the control from the controller 100, after performing focus control on the subject's eye (imaging site), the image of the subject's eye is acquired using the optical system 2. Specifically, the subject's eye is illuminated with the illumination light by the illumination optical system 20. The returning light of the illumination light from the subject's eye passes through the focusing lens and is received by the imaging device, in the imaging optical system 40. The controller 100 controls the data processor 200 to perform the above artifact removal processing on the image of the subject's eye acquired using the optical system 2, based on the dioptric power of the subject's eye corresponding to the focus control result for the optical system 2 described above.

Figure 1B:
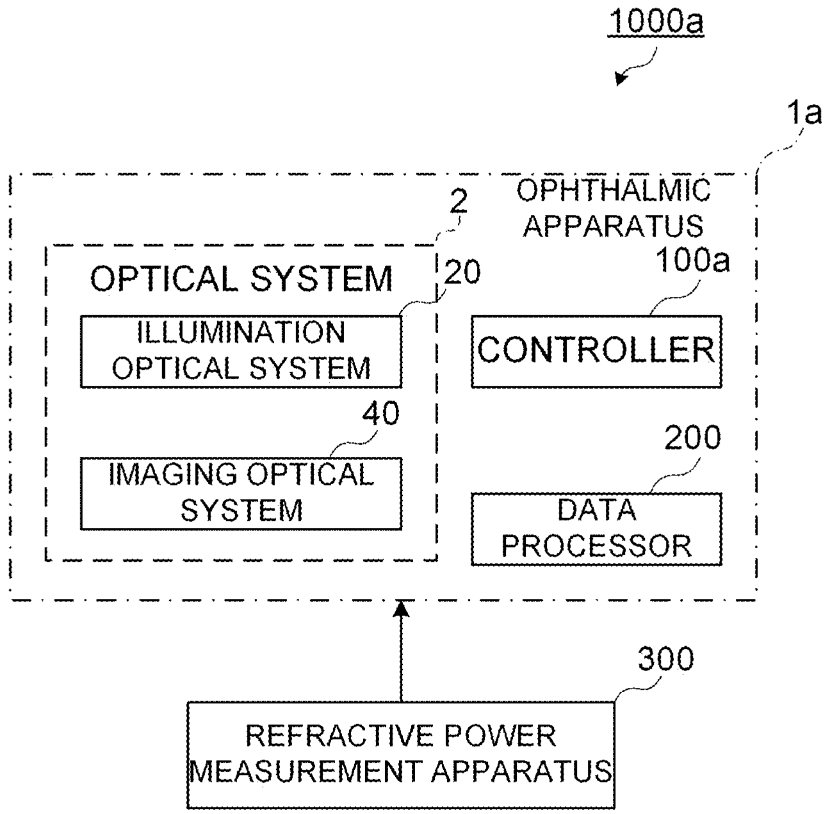
FIG. 1B is a schematic diagram illustrating a second configuration example of the ophthalmic system according to the embodiments.

FIG. 1B shows a functional block diagram of a second configuration example of the ophthalmic system according to the embodiments. In FIG. 1B, like reference numerals designate like parts as in FIG. 1A. The same description may not be repeated.

An ophthalmic system 1000*a* according to the second configuration example includes an ophthalmic apparatus 1*a* and a refractive power measurement apparatus 300. The ophthalmic apparatus 1*a*, similar to the ophthalmic apparatus 1, realizes the functions of the ophthalmic information processing apparatus and the functions of the ophthalmic imaging apparatus. The refractive power measurement apparatus 300 measures the dioptric power (refractive power) of the subject's eye using a known method as disclosed in, for example, Japanese Unexamined Patent Application No. 61-293430, Japanese Unexamined Patent Application Publication No. 2010-259495, or Japanese Unexamined Patent Application Publication No. 2017-42312.

The difference between the ophthalmic apparatus 1*a* and the ophthalmic apparatus 1 is that the ophthalmic apparatus 1*a* acquires the dioptric power of the subject's eye from the refractive power measurement apparatus 300. That is, the dioptric power of the subject's eye is acquired independently from the image of the subject's eye.

In such ophthalmic system 1000*a*, under the control from the controller 100*a*, the image of the subject's eye is acquired using the optical system 2. The controller 100*a* controls the data processor 200 to perform the above artifact removal processing on the image of the subject's eye acquired using the optical system 2, based on the dioptric power of the subject's eye acquired from the refractive power measurement apparatus 300.

Figure 1C:
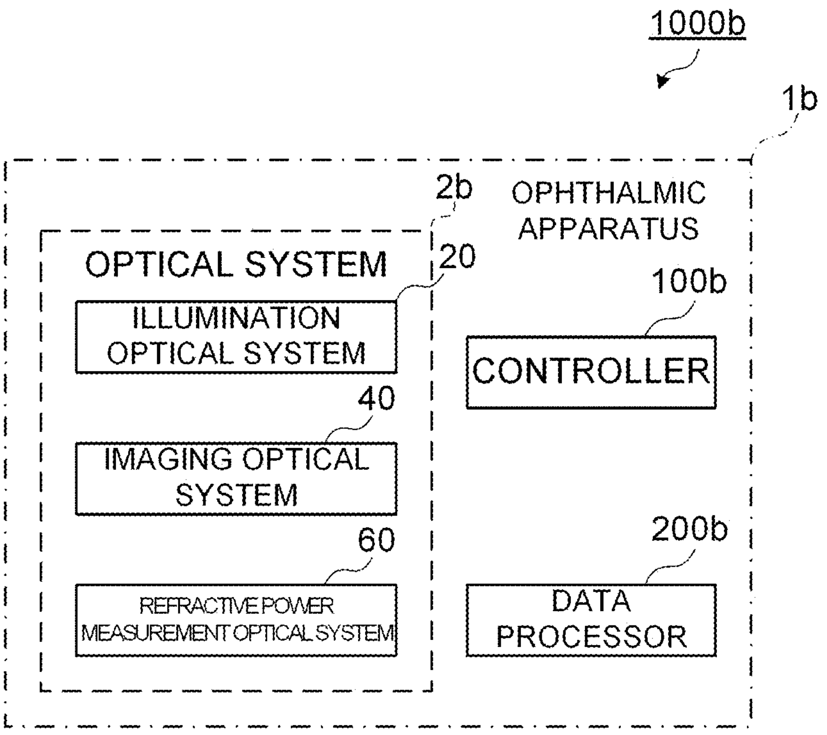
FIG. 1C is a schematic diagram illustrating a third configuration example of the ophthalmic system according to the embodiments.

FIG. 1C shows a functional block diagram of a third configuration example of the ophthalmic system according to the embodiments. In FIG. 1C, like reference numerals designate like parts as in FIG. 1A. The same description may not be repeated.

The ophthalmic system 1000*b* according to the third configuration example includes an ophthalmic apparatus 1*b*. The ophthalmic apparatus 1*b*, similar to the ophthalmic apparatus 1, realizes the functions of the ophthalmic information processing apparatus and the functions of the ophthalmic imaging apparatus.

The difference between the ophthalmic apparatus 1*b* and the ophthalmic apparatus 1 is that an optical system 2*b* in the ophthalmic apparatus 1*b* includes a refractive power measurement optical system 60 that realizes the functions of the refractive power measurement apparatus 300. A data processor 200*b* calculates the refractive power (dioptric power) of the subject's eye using a known method as disclosed in, for example, Japanese Unexamined Patent Application Publication No. 2017-42312, in addition to the functions of the data processor 200.

In such ophthalmic system 1000*b*, under the control from the controller 100*b*, the image of the subject's eye is acquired using the optical system 2*b* and the dioptric power of the subject's eye is calculated. The controller 100*b* controls the data processor 200*b* to perform the above artifact removal processing on the image of the subject's eye acquired using the optical system 2*b*, based on the dioptric power of the subject's eye calculated using the refractive power measurement optical system 60.

Figure 1D:
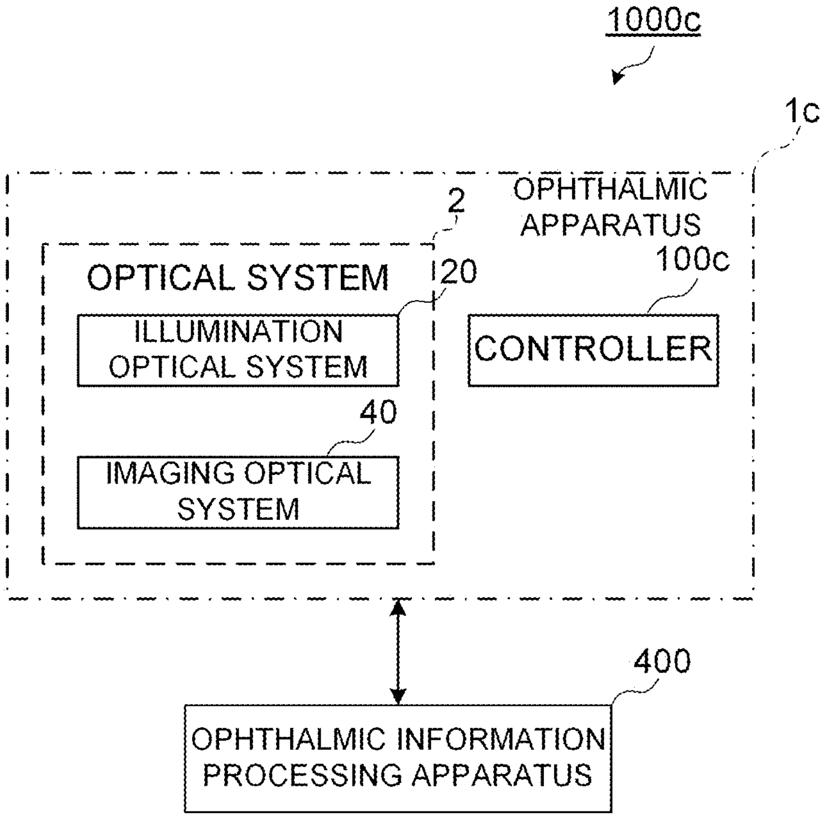
FIG. 1D is a schematic diagram illustrating a fourth configuration example of the ophthalmic system according to the embodiments.

FIG. 1D shows a functional block diagram of a fourth configuration example of the ophthalmic system according to the embodiments. In FIG. 1D, like reference numerals designate like parts as in FIG. 1A. The same description may not be repeated.

The ophthalmic system 1000*c* according to the fourth configuration example includes an ophthalmic apparatus 1*c* and an ophthalmic information processing apparatus 400. The ophthalmic apparatus 1*c* realizes the functions of the ophthalmic imaging apparatus. The ophthalmic information processing apparatus 400 realizes the functions of the ophthalmic information processing apparatus according to the embodiments.

The ophthalmic apparatus 1*c* includes the optical system 2 and a controller 100*c*. The optical system 2 includes the illumination optical system 20 and the imaging optical system 40. The controller 100*c* controls each part of the ophthalmic apparatus 1*c*. The controller 100*c*, similar to the controller 100, can identify the dioptric power of the subject's eye from the focus control result for the focusing lens in the imaging optical system 40. The functions of the controller 100*c* are realized by a processor, for example.

The ophthalmic information processing apparatus 400, similar to the data processor 200, identifies the correction region in the image of the subject's eye based on the dioptric power of the subject's eye. Here, the correction region corresponds to the shape of the artifact(s) depicted in the image of the subject's eye. And then, the ophthalmic information processing apparatus 400 performs artifact removal processing for correcting the correction region with the correction amount corresponding to the dioptric power of the subject's eye. The functions of such ophthalmic information processing apparatus 400 are realized by a processor.

In such ophthalmic system 1000*c*, under the control from the controller 100*c*, after performing focus control on the subject's eye (imaging site), the image of the subject's eye is acquired using the optical system 2. The ophthalmic information processing apparatus 400 performs the above artifact removal processing on the image of the subject's eye acquired using the optical system 2, based on the dioptric power of the subject's eye corresponding to the focus control result for the optical system 2 controlled by the controller 100*c*.

Figure 1E:
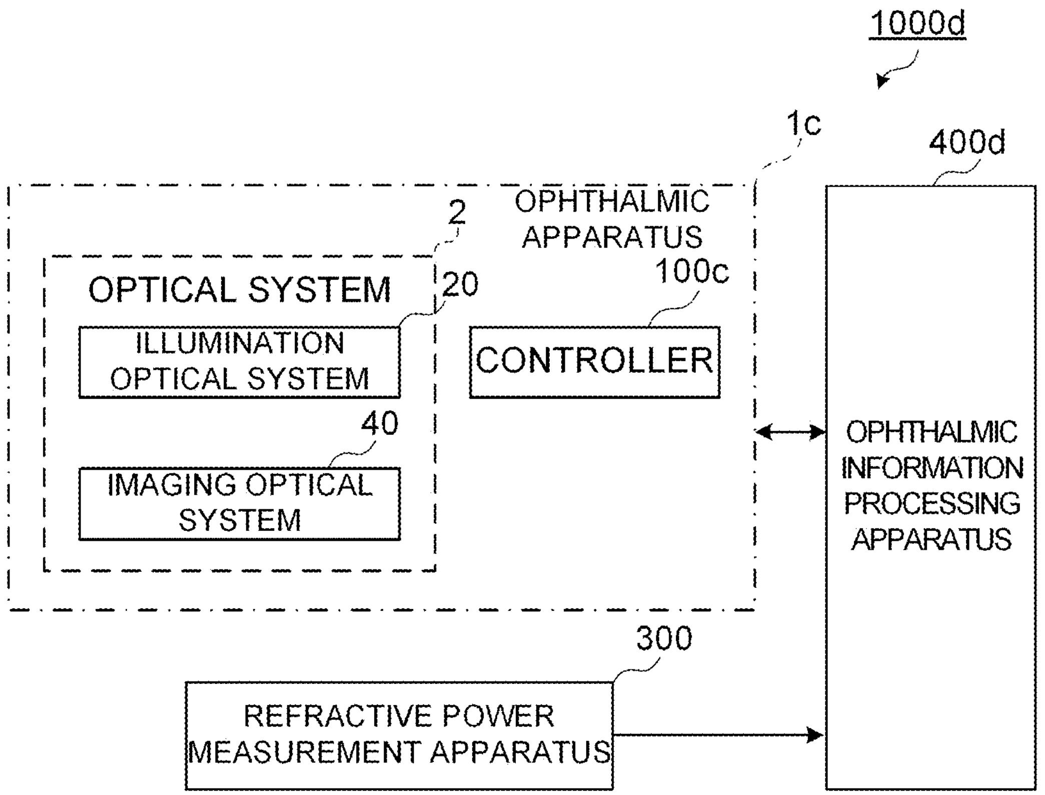
FIG. 1E is a schematic diagram illustrating a fifth configuration example of the ophthalmic system according to the embodiments.

FIG. 1E shows a functional block diagram of a fifth configuration example of the ophthalmic system according to the embodiments. In FIG. 1E, like reference numerals designate like parts as in FIG. 1B or FIG. 1D. The same description may not be repeated.

The ophthalmic system 1000*d* according to the fifth configuration example includes the ophthalmic apparatus 1*c*, the refractive power measurement apparatus 300 and an ophthalmic information processing apparatus 400*d*. The ophthalmic information processing apparatus 400*d*, similar to the ophthalmic information processing apparatus 400, realizes the functions of the ophthalmic information processing apparatus according to the embodiments.

The difference between the ophthalmic information processing apparatus 400*d* and the ophthalmic information processing apparatus 400 is that the ophthalmic information processing apparatus 400*d* acquires the dioptric power of the subject's eye from the refractive power measurement apparatus 300. That is, the dioptric power of the subject's eye is acquired independently from the image of the subject's eye.

In such ophthalmic system 1000*d*, under the control from the controller 100*c*, the image of the subject's eye is acquired using the optical system 2. The ophthalmic information processing apparatus 400*d* performs the above artifact removal processing on the image of the subject's eye acquired using the optical system 2 in the ophthalmic apparatus 1*c*, based on the dioptric power of the subject's eye acquired from the refractive power measurement apparatus 300.

Hereinafter, the ophthalmic information processing apparatus and the ophthalmic apparatus according to the embodiments will be described. In the following embodiments, the ophthalmic apparatus is assumed to realize the functions of the ophthalmic information processing apparatus according to the embodiments.

<Ophthalmic Apparatus>

Hereinafter, the ophthalmic apparatus according to the first configuration example will be specifically described as an example. However, the functions of the ophthalmic information processing apparatus according to the embodiments realized in the second to fifth configuration examples can be realized in the same manner as in the first configuration example.

For example, the ophthalmic apparatus according to the embodiments acquires the image of the subject's eye using slit-scan method. Specifically, the ophthalmic apparatus according to embodiments illuminates a predetermined site of the subject's eye while moving an irradiated position (irradiated range) of slit-shaped illumination light, and receives returning light from the predetermined site using an image sensor with a one-dimensional or two-dimensional array of light receiving elements. Light receiving result of the returning light is read out from the light receiving element(s) at light receiving position of the returning light corresponding to the irradiated position of the illumination light, in synchronization with the movement timing of the irradiated position of the illumination light. In some embodiments, the predetermined site is an anterior segment or a posterior segment. Examples of the anterior segment include a cornea, an iris, a crystalline lens, a ciliary body, and a ciliary zonule. Examples of the posterior segment include a vitreous body, and a fundus or the vicinity of the fundus (retina, choroid, sclera, etc.).

Hereinafter, a case will be mainly described where a fundus image is acquired and a black dot shadow depicted in the acquired fundus image is removed as an artifact.

[Configuration of Optical System]

Figure 2:
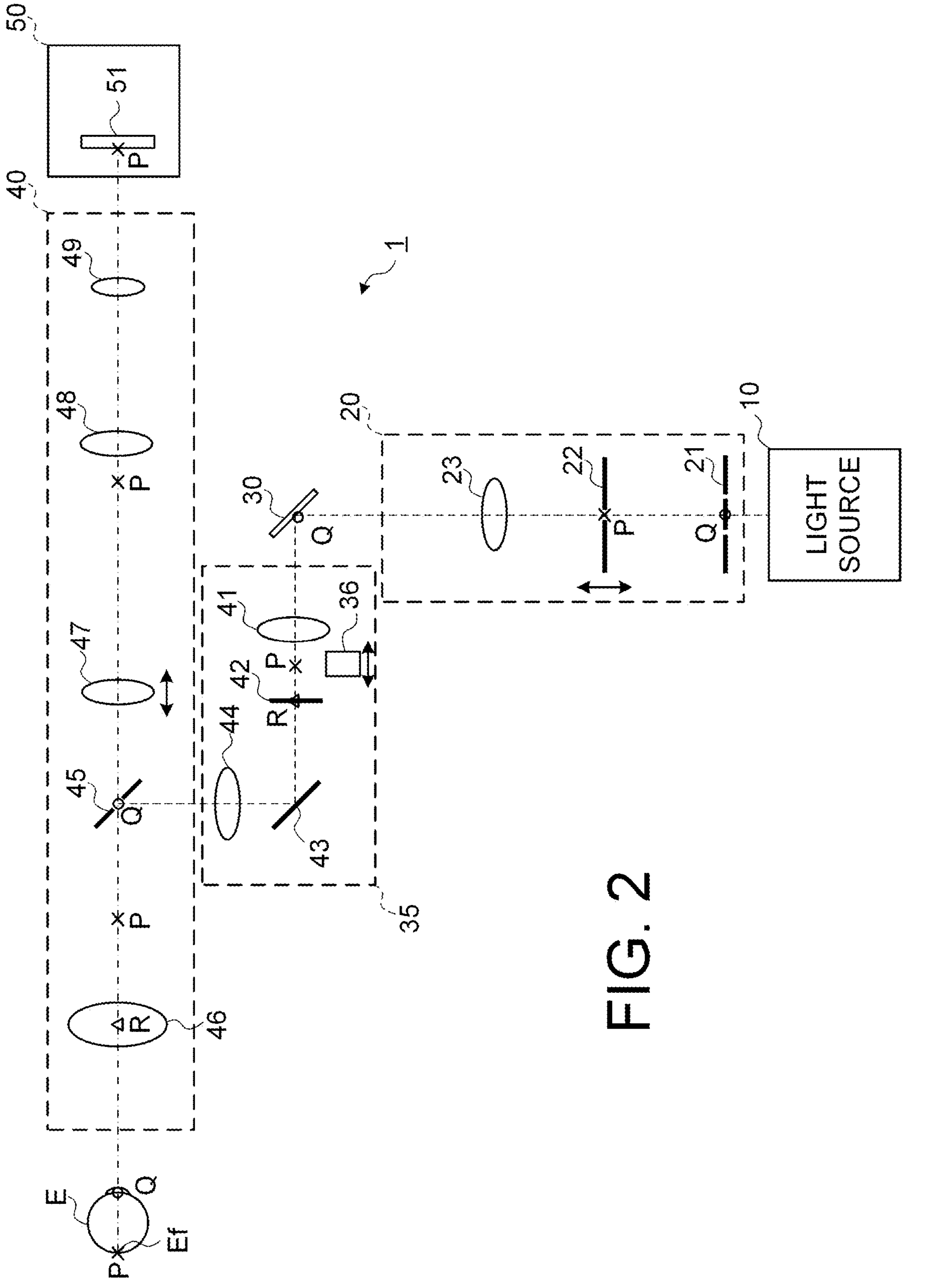
FIG. 2 is a schematic diagram illustrating an example of a configuration of an optical system of the ophthalmic apparatus according to the embodiments.
Figure 3:
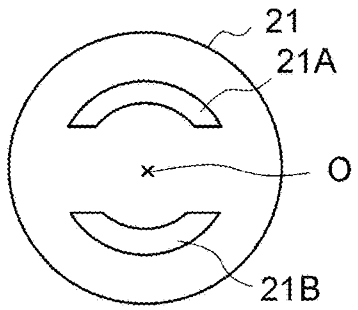
FIG. 3 is a schematic diagram illustrating an example of the configuration of the optical system of the ophthalmic apparatus according to the embodiments.
Figure 4:
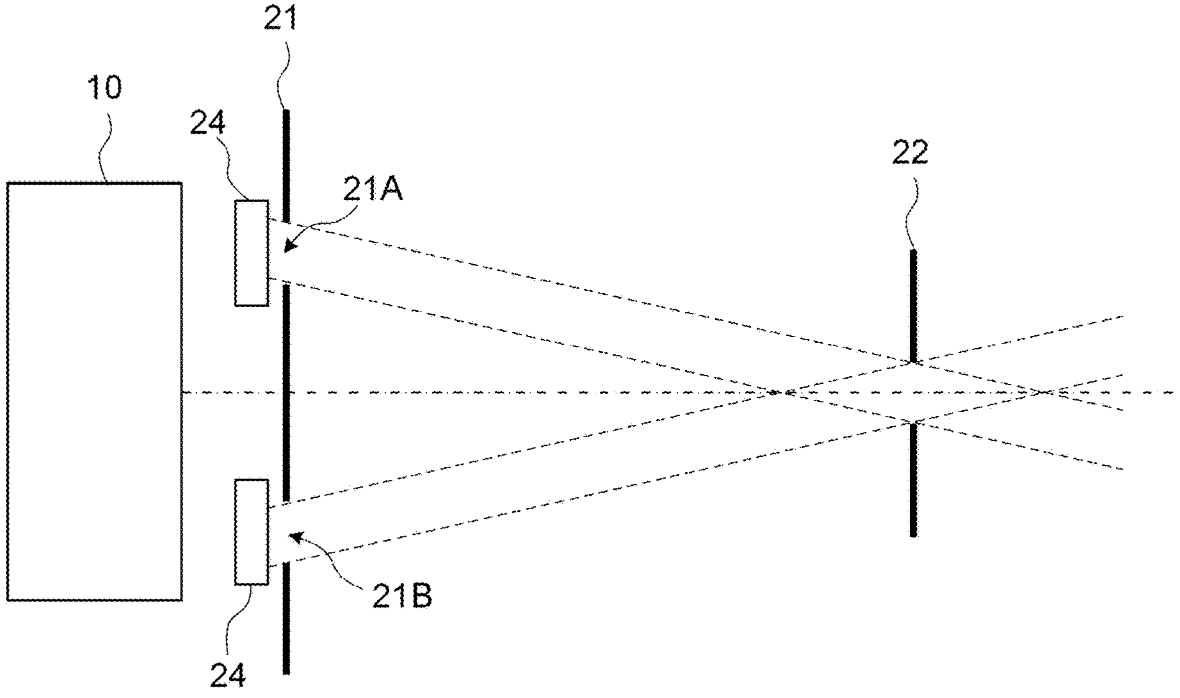
FIG. 4 is an explanatory diagram of the configuration of the ophthalmic apparatus according to the embodiments.

FIGS. 2 to 4 illustrate examples of a configuration of an optical system of the ophthalmic apparatus according to the embodiments. FIG. 2 represents an example of the configuration of the optical system of the ophthalmic apparatus 1 according to the embodiments. FIG. 3 schematically represents an example of the configuration of an iris aperture 21 in FIG. 2 when viewed from a direction of an optical axis O. FIG. 4 represents an example of the configuration of the iris aperture 21 in FIG. 2 and a slit 22 in FIG. 2 when viewed from the side or top. In FIG. 2, a position conjugate optically to a fundus Ef of a subject's eye E is illustrated as a fundus conjugate position P, a position conjugate optically to an iris of the subject's eye E is illustrated as an iris conjugate position Q, and a position conjugate optically to a black dot is illustrated as a black dot conjugate position R. In FIGS. 2 to 4, like parts are designated by like reference numerals as in FIG. 1A and repetitious description of such parts may not be provided.

The ophthalmic apparatus 1 includes a light source 10, the illumination optical system 20, an optical scanner 30, a projection optical system 35, the imaging optical system 40, and an imaging device 50. In some embodiments, the illumination optical system 20 includes at least one of the light source 10, the optical scanner 30, and the projection optical system 35. In some embodiments, the imaging optical system 40 includes the imaging device 50. In some embodiments, the projection optical system 35 or the illumination optical system 20 includes the optical scanner 30.

(Light Source 10)

The light source 10 includes a visible light source that generates light in the visible region. For example, the light source 10 generates light having a central wavelength in the wavelength range of 420 nm to 700 nm. This type of light source 10 includes, for example, an LED (Light Emitting Diode), an LD (Laser Diode), a halogen lamp, or a xenon lamp. In some embodiments, the light source 10 includes a white light source or a light source capable of outputting light with each color component of RGB. In some embodiments, the light source 10 includes a light source capable of switching to output the light in infrared region or the light in visible region. The light source 10 is arranged at a position non-conjugate optically to the fundus Ef and the iris, respectively.

In some embodiments, the imaging optical system 40 described below includes an optical element such as a correction lens that can be inserted into and removed from an optical path of the returning light in accordance with the wavelength range (central wavelength) of the light emitted from the light source 10, in order to image the returning light from the subject's eye on an imaging surface of the image sensor 51 in the imaging device 50 in the focusing state regardless of the wavelength range (center wavelength) of the returning light from the subject's eye E.

(Illumination Optical System 20)

The illumination optical system 20 generates slit-shaped illumination light using the light from the light source 10. The illumination optical system 20 guides the generated illumination light to the optical scanner 30.

The illumination optical system 20 includes the iris aperture 21, the slit 22, and a relay lens 23. The light from the light source 10 passes through the aperture(s) formed in the iris aperture 21, passes through the aperture formed in the slit 22, and is transmitted through the relay lens 23. The relay lens 23 includes one or more lenses. The light transmitted through the relay lens 23 is guided to the optical scanner 30.

(Iris Aperture 21)

The iris aperture 21 (specifically, aperture(s) described below) can be arranged at a position substantially conjugate optically to the iris (pupil) of a subject's eye E. In the iris aperture 21, one or more apertures are formed at position(s) away from the optical axis O. For example, as shown in FIG. 3, apertures 21A and 21B having a predetermined thickness along a circumferential direction centered on the optical axis O are formed in the iris aperture 21. The aperture(s) formed in the iris aperture 21 defines an incident position (incident shape) of the illumination light on the iris of the subject's eye E. For example, by forming the apertures 21A and 21B as shown in FIG. 3, when the pupil center of the subject's eye E is arranged on the optical axis O, the illumination light can enter into the eye from positions deviated from the pupil center (specifically, point-symmetrical positions centered on the pupil center), In some embodiments, as shown in FIG. 4, an optical element 24 is arranged between the light source 10 and the iris aperture 21. The optical element 24 can be arranged at a position substantially conjugate optically to the iris. The optical element 24 deflects the light from the light source. The optical element 24 deflects the light from the light source 10 so that the light amount distribution in a direction connecting the aperture 21A (or aperture 21B) formed in the iris aperture 21 and an aperture formed in the slit 22 is maximized Examples of such optical element include a prism, a microlens array, or a Fresnel lens. In FIG. 4, the optical element 24 is provided for each aperture formed in the iris aperture 21. However, a single element may be configured to deflect the light passing through the apertures 21A and 21B formed in the iris aperture 21.

Further, the light amount distribution of the light passing through the aperture(s) formed in the iris aperture 21 can be changed by changing a relative position between the light source and the aperture(s) formed in the iris aperture 21.

(Slit 22)

The slit 22 (specifically, aperture(s) described below) can be arranged at a position substantially conjugate optically to the fundus Ef of the subject's eye E. For example, in the slit 22, the aperture is formed extending in a direction corresponding to a line direction (row direction) that is read out from the image sensor 51 described below using the rolling shutter method. The aperture formed in the slit 22 defines an irradiated pattern of the illumination light on the fundus Ef of the subject's eye E.

The slit 22 can be moved in the optical axis direction of the illumination optical system using a movement mechanism (movement mechanism 22D described below). The movement mechanism moves the slit 22 in the optical axis direction, under the control from the controller 100 described below. For example, the controller 100 described below controls the movement mechanism in accordance with the state of the subject's eye E. This allows to move the position of the slit 22 in accordance with the state of the subject's eye E (specifically, the dioptric power (refractive power) or the shape of the fundus Ef).

In some embodiments, the slit 22 is configured so that at least one of the position of the aperture and the shape of the aperture can be changed in accordance with the state of the subject's eye E without being moved in the optical axis direction. The function of the slit 22 with this configuration is, for example, realized by a liquid crystal shutter.

The light from the light source 10 that has passed through the aperture(s) formed in the iris aperture 21 is output as the slit-shaped illumination light by passing through the aperture formed in the slit 22. The slit-shaped illumination light is transmitted through the relay lens 23, and is guided to the optical scanner 30.

(Optical Scanner 30)

The optical scanner 30 is placed at a position substantially conjugate optically to the iris of the subject's eye E. The optical scanner 30 deflects the slit-shaped illumination light transmitted through the relay lens 23 (slit-shaped light passing through the aperture formed in the slit 22). Specifically, the optical scanner 30 deflects the slit-shaped illumination light for sequentially illuminating a predetermined illumination range of the fundus Ef to guide the illumination light to the projection optical system 35, while changing the deflection angle within a predetermined deflection angle range with the iris or the vicinity of the iris of the subject's eye E as a scan center position. The optical scanner 30 can deflect the illumination light one-dimensionally or two-dimensionally.

In case that the optical scanner 30 deflects the illumination light one-dimensionally, the optical scanner 30 includes a galvano scanner that deflects the illumination light within a predetermined deflection angle range with reference to a predetermined deflection direction. In case that the optical scanner 30 deflects the illumination light two-dimensionally, the optical scanner 30 includes a first galvano scanner and a second galvano scanner. The first galvano scanner deflects the illumination light so as to move the irradiated position of the illumination light in a horizontal direction orthogonal to the optical axis of the illumination optical system 20. The second galvano scanner deflects light deflected by the first galvano scanner so as to move the irradiated position of the illumination light in a vertical direction orthogonal to the optical axis of the illumination optical system 20. Examples of scan mode for moving the irradiated position of the illumination light using the optical scanner 30 include a horizontal scan, a vertical scan, a cross scan, a radial scan, a circle scan, a concentric scan, and a helical (spiral) scan.

(Projection Optical System 35)

The projection optical system 35 guides the illumination light deflected by the optical scanner 30 to the fundus Ef of the subject's eye E. In the embodiments, the projection optical system 35 guides the illumination light deflected by the optical scanner 30 to the fundus Ef through an optical path coupled with an optical path of the imaging optical system 40 by a perforated mirror 45 as the optical path coupling member described below.

The projection optical system 35 includes a relay lens 41, a black dot (black dot plate) 42, a reflective mirror 43, and a relay lens 44. Each of the relay lenses 41 and 44 includes one or more lenses. In some embodiments, the projection optical system 35 further includes a focus indicator optical system 36.

(Black Dot 42)

The black dot 42 is arranged at a position substantially conjugate optically to a position of the center ghost formed by reflection of the illumination light on the lens surface of the objective lens 46. In the configuration of FIG. 2, the black dot 42 is arranged at a position substantially conjugate optically to a position of an image of the perforated mirror 45 (photographic aperture image) formed by the reflection light of the illumination light from the lens surface of the objective lens 46.

(Focus Indicator Optical System 36)

The focus indicator optical system 36 projects focus indicator(s) onto the fundus Ef of the subject's eye E. For example, the focus indicator optical system 36 includes a focus indicator light source, a split indicator plate, a two-hole diaphragm, and an indicator projection lens.

The light output from the focus indicator light source (i.e., focus light) is split into two light beams by the split indicator plate, passes through the two-hole diaphragm, and is projected onto the fundus Ef of the subject's eye E by the indicator projection lens. When performing focus adjustment, for example, a reflective surface of a reflective rod is obliquely set on an optical path of the projection optical system 35 (illumination optical system 20) (e.g., between the relay lens 41 and the black dot 42), the focus indicator light that has passed through the indicator projection lens travels through the same optical path as the illumination light, and is projected onto the fundus Ef of the subject's eye E. The reflective rod may be capable of being positioned at the fundus conjugate position P on the optical path of the projection optical system 35, for example.

Fundus reflection light of the focus indicator light passes through the hole formed in the perforated mirror 45, and is detected by the image sensor 51 in the imaging device 50. Light receiving image (split indicator) captured by the image sensor 51 is displayed on a display means not shown in the figure. For example, the controller 100 described below analyzes the position of the split indicator according to the Scheiner principle, and moves each of the focusing lens 47 and the focus indicator optical system 46, which are described below, in the optical axis direction to perform focusing (automatic focus function). Alternatively, the user may perform focusing manually while visually checking the split indicator.

With such projection optical system 35, the illumination light deflected by the optical scanner 30 is transmitted through the relay lens 41, passes through the black dot 42, is reflected by the reflective mirror 43 toward the perforated mirror 45. When performing focus adjustment, the focus indicator light from the focus indicator optical system 36, which is reflected on the reflective surface of the reflective rod obliquely set against the optical path of the illumination light, passes through the black dot 42, and is reflected by the reflective mirror 43 toward the perforated mirror 45.

(Imaging Optical System 40)

The imaging optical system 40 guides the illumination light (or focus indicator light) that has been guided through the projection optical system 35 to the fundus Ef of the subject's eye E, and also guides the returning light of the illumination light from the fundus Ef (or fundus reflection light of the focus indicator light) to the imaging device 50.

In the imaging optical system 40, an optical path of the illumination light from the projection optical system 35 and an optical path of the returning light of the illumination light from the fundus Ef are coupled. By using the perforated mirror 45 as an optical path coupling member to couple these optical paths, it enables pupil division between the illumination light and the returning light of the illumination light.

The imaging optical system 40 includes the perforated mirror 45, the objective lens 46, the focusing lens 47, a relay lens 48, and an imaging lens 49. The relay lens 48 includes one or more lenses.

(Perforated Mirror 45)

In the perforated mirror 45, the hole is formed. The hole is arranged on the optical axis of the imaging optical system 40. The hole of the perforated mirror 45 is arranged at a position substantially conjugate optically to the iris of the subject's eye E. The perforated mirror 45 reflects the illumination light from the projection optical system 35 toward the objective lens 46, on the peripheral region of the hole. The perforated mirror 45 with this configuration functions as an imaging aperture (photographic stop (diaphragm)).

That is, the perforated mirror 45 is configured to couple the optical path of the illumination optical system 20 (projection optical system 35) and the optical path of the imaging optical system 40 arranged in a direction of the optical axis passing through the hole, and also to guide the illumination light reflected on the peripheral region of the hole to the fundus Ef.

(Focusing Lens 47)

The focusing lens 47 can be moved in an optical axis direction of the imaging optical system 40 using a movement mechanism (not shown). The movement mechanism moves the focusing lens 47 in the optical axis direction under the control from the controller 100 described below. This allows to image the returning light of the illumination light passing through the hole of the perforated mirror 45 on the light receiving surface of the image sensor 51 in the imaging device 50 in accordance with the state of the subject's eye E.

In the imaging optical system 40 with this configuration, the illumination light from the projection optical system 35 (or focus indicator light) is reflected toward the objective lens 46 on the peripheral region of the hole formed in the perforated mirror 45. The illumination light reflected on the peripheral region of perforated mirror 45 is refracted by the objective lens 46, enters into the eye through the pupil of the subject's eye E, and illuminates the fundus Ef of the subject's eye E. In the same way, the focus indicator light reflected on the peripheral region of perforated mirror 45 is refracted by the objective lens 46, enters into the eye through the pupil of the subject's eye E, and is projected onto the fundus Ef of the subject's eye E.

The returning light of the illumination light from the fundus Ef (or fundus reflection light of the focus indicator light) is refracted by the objective lens 46, passes through the hole of the perforated mirror 45, is transmitted through the focusing lens 47, is transmitted through the relay lens 48, and is imaged on the light receiving surface of the image sensor 51 in the imaging device 50 through the imaging lens 49.

(Imaging Device 50)

The imaging device 50 includes the image sensor 51 receiving the returning light of the illumination light that has been guided from the fundus Ef of the subject's eye E through the imaging optical system 40. The imaging device 50 can perform readout control of the light receiving result of the returning light under the control from the controller 100 described below.

(Image Sensor 51)

The image sensor 51 realizes the function as a pixelated photodetector. The light receiving surface (detecting surface, imaging surface) of the image sensor 51 can be arranged at a position substantially conjugate optically to the fundus Ef.

The light receiving result(s) obtained using the image sensor 51 is/are read out using a rolling shutter method under the control from the controller 100 described below.

The image sensor 51 with this configuration includes the CMOS image sensor. In this case, the image sensor 51 includes a plurality of pixels (light receiving elements). The plurality of pixels includes a plurality of pixel groups arranged in a column direction. Each of the plurality of pixel groups includes pixels arranged in a row direction. Specifically, the image sensor 51 includes a plurality of pixels arranged two-dimensionally, a plurality of vertical signal lines, and a horizontal signal line. Each pixel includes a photodiode (light receiving element), and a capacitor. The vertical signal lines are provided for each pixel group in the column direction (vertical direction) orthogonal to the row direction (horizontal direction). Each of the vertical signal lines is selectively electrically connected to the pixel group in which the electrical charge corresponding to the light receiving result is accumulated. The horizontal signal line is selectively electrically connected to the vertical signal lines. Each of the pixels accumulates the electrical charge corresponding to the light receiving result of the returning light. The accumulated electrical charge is read out sequentially for each pixel group in the row direction, for example. For example, for each line in the row direction, a voltage corresponding to the electrical charge accumulated in each pixel is supplied to the vertical signal line. The vertical signal lines are selectively electrically connected to the horizontal signal line. By performing readout operation for each line in the row direction described above sequentially in the vertical direction, the light receiving results of the plurality of pixels arranged two-dimensionally can be read out.

By capturing (reading out) the light receiving results of the returning light using the rolling shutter method for this type of image sensor 51, the light receiving image corresponding to the desired virtual opening shape extending in the row direction is acquired. Such control is disclosed in, for example, U.S. Pat. No. 8,237,835.

Figure 5:
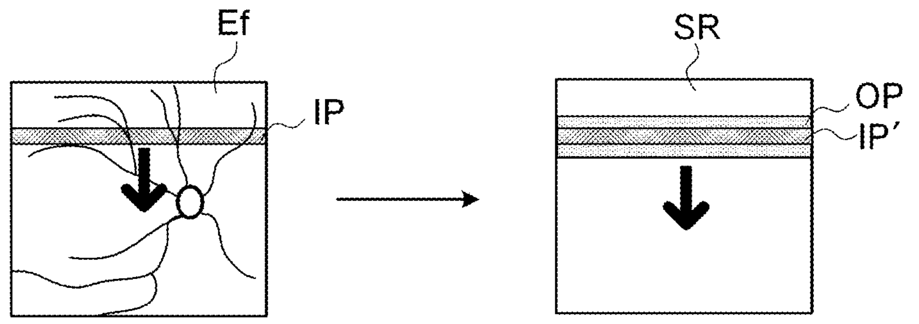
FIG. 5 is an explanatory diagram of an operation of the ophthalmic apparatus according to the embodiments.

FIG. 5 shows a diagram explaining the operation of the ophthalmic apparatus 1 according to the embodiments. FIG. 5 schematically represents an irradiated range IP of the slit-shaped illumination light irradiated on the fundus Ef and a virtual opening range OP on the light receiving surface SR of the image sensor 51.

For example, the controller 100 described below deflects the slit-shaped illumination light formed by the illumination optical system 20, using the optical scanner 30. Thereby, the irradiated range IP of the slit-shaped illumination light is sequentially moved in a direction (for example, the vertical direction) orthogonal to the slit direction (for example, the row direction, the horizontal direction) on the fundus Ef.

On the light receiving surface SR of the image sensor 51, by changing the pixels to be read out in units of lines by the controller 100 described below, the virtual opening range OP is set. The opening range OP is preferable to be the light receiving range IP' of the returning light of the illumination light on the light receiving surface SR or wider than the light receiving range IP'. The controller 100 described below performs the movement control of the opening range OP in synchronization with the movement control of the irradiated range IP of the illumination light. Thereby, without being affected by unnecessary scattered light, high quality images of the fundus Ef with strong contrast can be acquired using a simple configuration.

Figure 6:
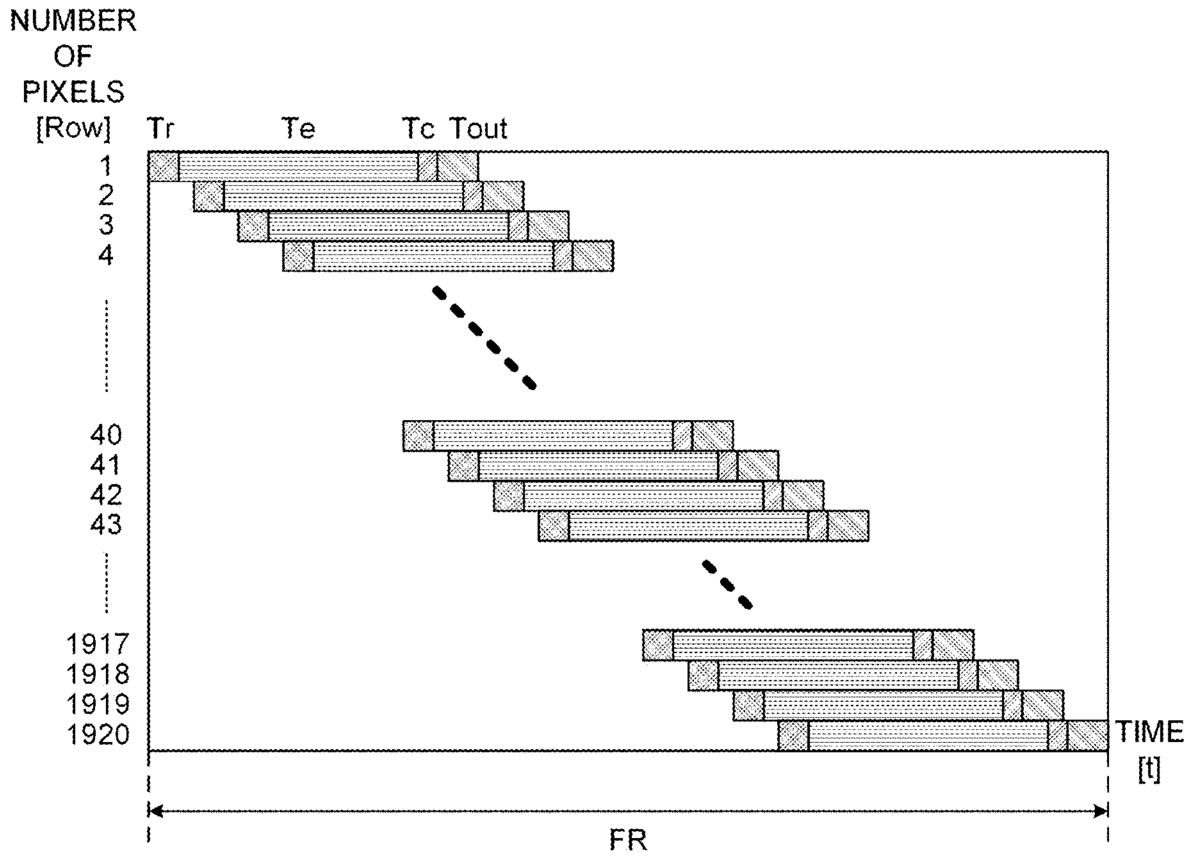
FIG. 6 is an explanatory diagram of the operation of the ophthalmic apparatus according to the embodiments.
Figure 7:
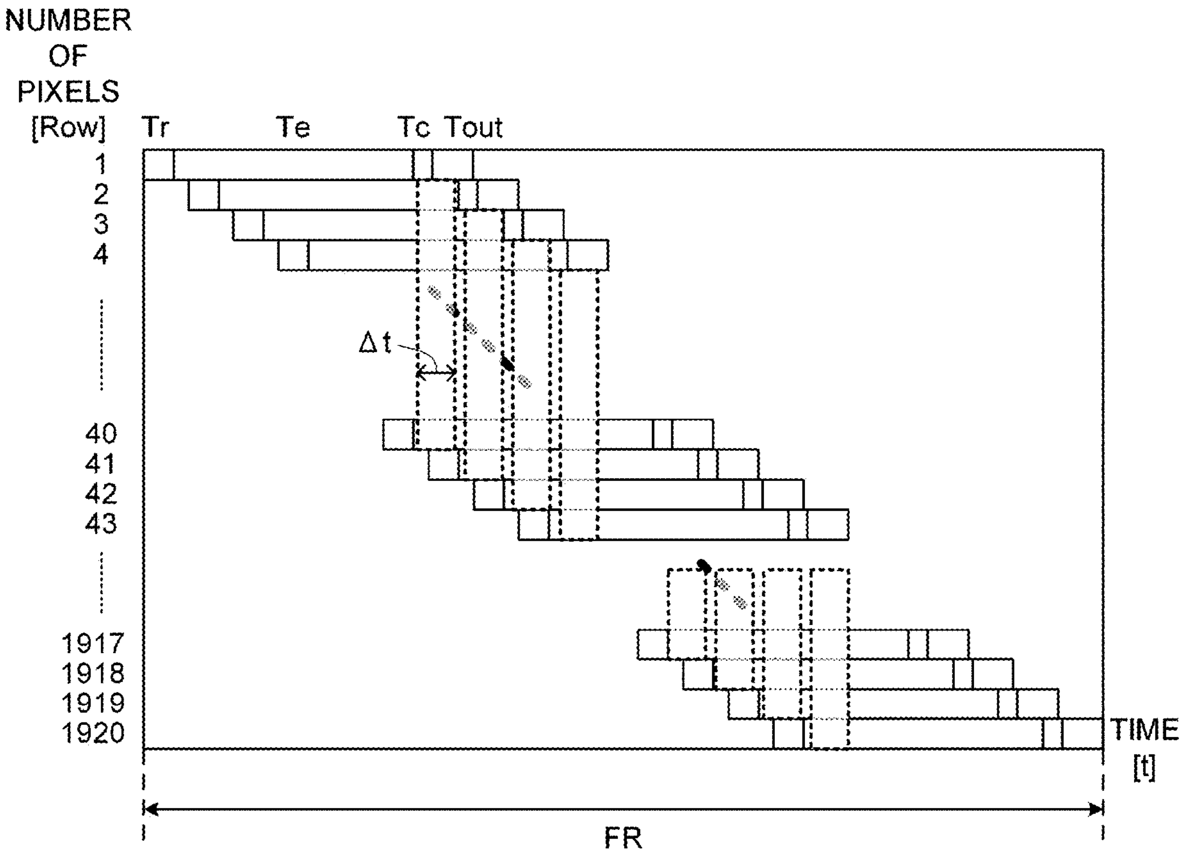
FIG. 7 is an explanatory diagram of the operation of the ophthalmic apparatus according to the embodiments.

FIGS. 6 and 7 schematically show examples of the control timing of the rolling shutter method for the image sensor 51. FIG. 6 represents an example of the timing of the readout control for the image sensor 51. FIG. 7 represents the timing of the movement control for the irradiated range IP (the light receiving range IP') superimposed on the timing of the readout control in FIG. 6. In FIGS. 6 and 7, the horizontal axis represents the number of rows in the image sensor 51, and the vertical axis represents time.

In addition, in FIGS. 6 and 7, for convenience of explanation, it is assumed that the number of rows in the image sensor 51 is 1920. However, the configuration according to the embodiments is not limited to the number of rows. Further, in FIG. 7, for convenience of explanation, it is assumed that the slit width (width in the row direction) of the slit-shaped illumination light is 40 rows.

The readout control in the row direction includes the reset control, the exposure control, the charge transfer control, and the output control. The reset control is a control that initializes the amount of electrical charge accumulated in the pixels in the row direction. The exposure control is a control that illuminates light on the photodiode and accumulates the electrical charge corresponding to the amount of received light in the capacitor. The charge transfer control is a control that transfers the amount of the electrical charge accumulated in the pixel to the vertical signal line. The output control is a control that outputs the amount of the electrical charge accumulated in the plurality of vertical signal lines via the horizontal signal line. That is, as shown in FIG. 6, the readout time T for reading out the electrical charge accumulated in the pixels in the row direction is the sum of the time Tr required for the reset control, the time Te required for the exposure control (exposure time), the time Tc required for the charge transfer control, and the time Tout required for the output control.

In FIG. 6, by shifting the readout start timing (start timing of time Tc) in units of rows, the light receiving results (amount of electrical charge) accumulated in the pixels in the desired range in the image sensor 51 are acquired. For example, in case that the pixel range shown in FIG. 6 is for a single frame of the image, the frame rate FR is determined uniquely.

In this embodiment, the irradiated position of the illumination light on the fundus Ef, the illumination light having a slit width for a plurality of rows, is sequentially shifted in a direction corresponding to the column direction on the fundus Ef.

For example, as shown in FIG. 7, at each predetermined shift time Δt, the irradiated position of the illumination light on the fundus Ef is shifted in row units in the direction corresponding to the column direction. The shift time Δt is obtained by dividing the exposure time Te of the pixel in the image sensor 51 by the slit width (e.g., 40) of the illumination light (Δt=Te/40). Synchronized with this movement timing of this irradiated position, the readout start timing of each row of pixels is delayed and is started for each row in units of shift time Δt. This allows to acquired high quality images of the fundus Ef with strong contrast in a short time with a simple control.

In some embodiments, the image sensor 51 is configured using one or more line sensors.

In the ophthalmic apparatus 1 having the above configuration, an artifact called black dot shadow may occur in the fundus image caused by the black dot 42 placed so as to remove the center ghost, the black dot 42 blocking a part of the illumination light for uniformly illuminating the fundus Ef. In particular, the shape of the black dot shadow, the intensity (shadow density) of the black dot shadow, and the occurrence location of the black dot shadow in the fundus image vary according to the spread of the illumination light flux.

Figure 8:
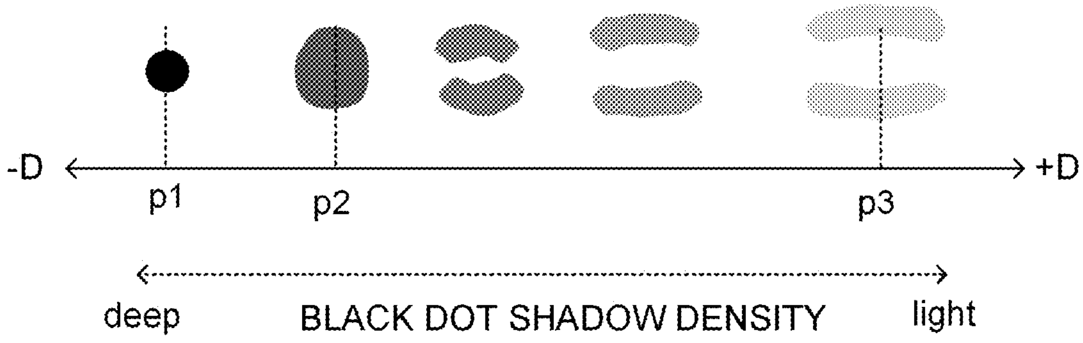
FIG. 8 is an explanatory diagram of the ophthalmic apparatus according to the embodiments.

FIG. 8 schematically shows the changes in the shape and intensity of the black dot shadow with respect to changes in the spread of the illumination light flux. In FIG. 8, the horizontal axis represents the diopter positions corresponding to the spread of the illumination light.

At a position p1, which is the black dot conjugate position, the image of the black dot 42 itself becomes the black dot shadow, and the density of the black dot shadow is the deepest. The farther away from the position p1, the wider the illumination light flux spreads. Therefore, the position in the image, the shape, and the density of the black dot shadow change. For example, at a position p2, which is the fundus conjugate position, the diameter of the black dot shadow becomes larger and the density of the black dot shadow becomes lighter. Furthermore, as the illumination light flux spreads, the black dot shadow separates into two images corresponding to the apertures 21A and 21B formed in the iris aperture 21 and the shapes of the shadows change. At a position p3, which is the iris conjugate position, the shadows become two black dot shadows with light shadow density. Although not illustrated in FIG. 8, the position of the black dot shadow in the fundus image also changes in accordance with the spread of the illumination light flux.

In other words, since the spread of the illumination light flux changes in accordance with the dioptric power of the subject's eye, the position, shape, and intensity of the black dot shadow in the image changes in accordance with the dioptric power of the subject's eye. Since the spread of the illumination light flux is determined by the optical condition(s) in the optical system, the position, shape, and intensity of the black dot shadow in the fundus image can be identified when the shape of the black dot 42 (black dot diameter) and the dioptric power of the subject's eye are known. By correcting the luminance value(s) of the pixel(s) to be higher in accordance with the position, shape, and intensity of the black dot shadow identified in the fundus image, the black dot shadow can be removed with high precision or the effect of the black dot shadow can be significantly reduced.

Similarly, even when the artifact is the center ghost, the position, shape, and intensity of the center ghost in the fundus image change in accordance with the dioptric power of the subject's eye, since the spread of the illumination light flux changes in accordance with the dioptric power of the subject's eye. Since the spread of the illumination light flux is determined by the optical condition(s) in the optical system, by correcting the luminance value(s) of the pixel(s) to be lower in accordance with the position, shape, and intensity of the center ghost identified in the fundus image, the center ghost can be removed with high precision or the effect of the center ghost can be significantly reduced.

[Configuration of Control System]

Figure 9:
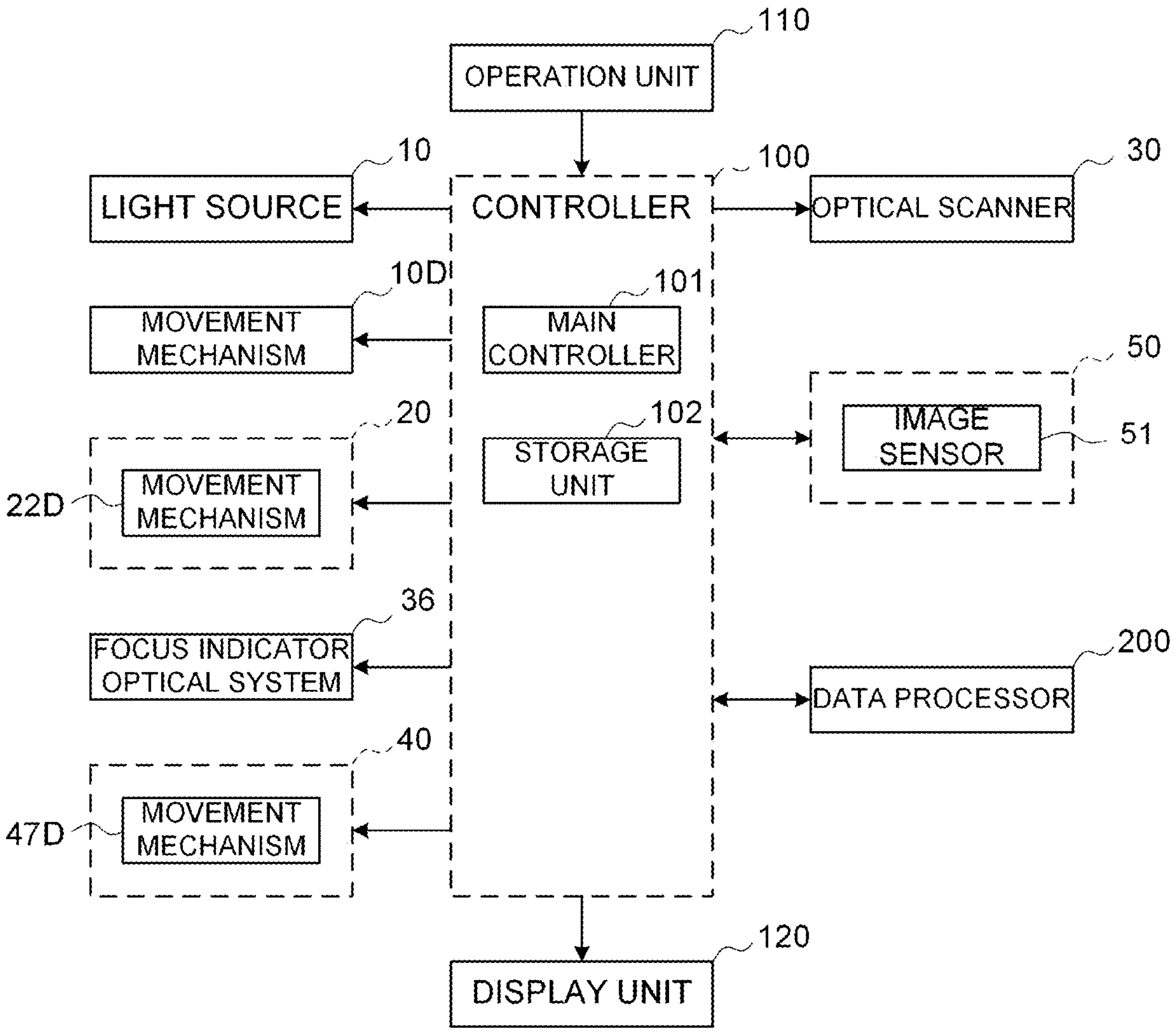
FIG. 9 is a schematic diagram illustrating an example of a configuration of a control system of the ophthalmic apparatus according to the embodiments.

FIG. 9 shows a block diagram of an example of a configuration of a control system of the ophthalmic apparatus 1 according to the embodiments. In FIG. 9, like reference numerals designate like parts as in FIG. 2, and the redundant explanation may be omitted as appropriate.

As shown in FIG. 9, the control system (processing system) of the ophthalmic apparatus 1 is configured with the controller 100 as a center. It should be noted that at least a part of the configuration of the control system may be included in the ophthalmic apparatus 1.

(Controller 100)

The controller 100 controls each part of the ophthalmic apparatus 1. The controller 100 includes a main controller 101 and a storage unit 102. The main controller 101 includes a processor and executes the control processing of each part of the ophthalmic apparatus 1 by executing processing according to the program(s) stored in the storage unit 102.

(Main Controller 101)

The main controller 101 performs control for the light source 10 and a movement mechanism 10D, control for the illumination optical system 20, control for the focus indicator optical system 36, control for the optical scanner 30, control for the imaging optical system 40, control for the imaging device 50, and control for the data processor 200.

The control for the light source 10 includes switching the light source on and off (or switching the wavelength region of the light), and changing the light amount of the light source.

The movement mechanism 10D changes at least one of the position of the light source and the orientation of the light source 10 using a known mechanism. The main controller 101 can change at least one of a relative position of the light source 10 to the iris aperture 21 and the slit 22, and a relative orientation of the light source 10 to the iris aperture 21 and the slit 22.

The control for the illumination optical system 20 includes control for a movement mechanism 22D. The movement mechanism 22D moves the slit 22 in the optical axis direction of the illumination optical system 20. The main controller 101 controls the movement mechanism 22D in accordance with the state of the subject's eye E to arrange the slit 22 at the position corresponding to the state of the subject's eye E. Examples of the state of the subject's eye E includes a shape of the fundus Ef, a dioptric power (refractive power), and an axial length. The dioptric power, for example, can be identified from the position on the optical axis of the focusing lens 47 when it is determined to be in the focusing state by the focus control using the focus indicator optical system 36 and the focusing lens 47, as described below. Alternatively, the dioptric power can be acquired from a known eye refractive power measurement apparatus as disclosed in Japanese Unexamined Patent Application No. 61-293430 or Japanese Unexamined Patent Application Publication No. 2010-259495, for example. The axial length can be obtained from a known axial length measurement apparatus or a measurement value acquired by an optical coherence tomography.

For example, the storage unit 102 stores first control information. In the first control information, the positions of the slit 22 on the optical axis of the illumination optical system are associated with the dioptric powers in advance. The main controller 101 identifies the position of the slit 22 corresponding to the dioptric power by referring to the first control information, and controls the movement mechanism 22D so as to arrange the slit 22 at the identified position.

Here, as the slit 22 moves, the light amount distribution of the light passing through the aperture formed in the slit 22 changes. In this case, as described above, the main controller 101 can control the movement mechanism 10D to change at least one of the position of the light source 10 and the orientation of the light source 10.

Figure 10:
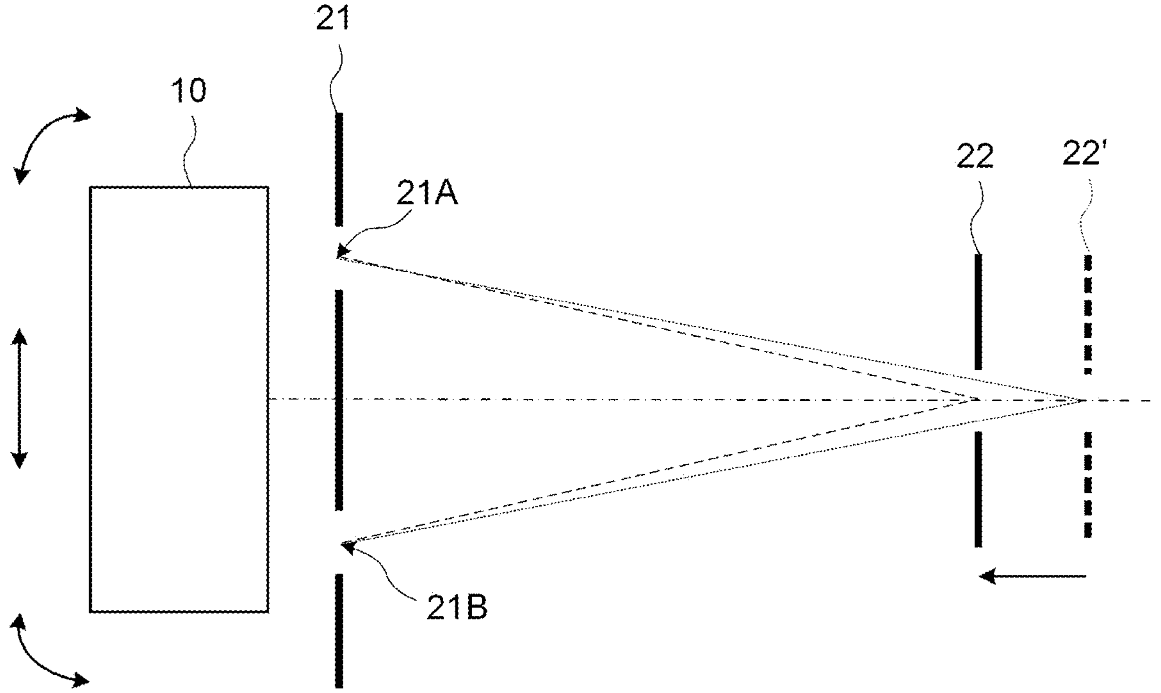
FIG. 10 is an explanatory diagram of the operation of the ophthalmic apparatus according to the embodiments.

FIG. 10 shows a diagram describing the control content of the main controller 101 according to the embodiments. FIG. 10 schematically represents a positional relationship between the light source 10, the iris aperture 21, and the slit 22 when viewed from the side or top. In FIG. 10, parts similar to those in FIGS. 2 to 4 are denoted by the same reference symbols, and description thereof is omitted as appropriate.

As described above, the position of the slit 22 is moved from the position of the slit 22' before the movement according to the state of the subject's eye E. Thereby, the light amount distribution of the light passing through the aperture formed in the slit 22 changes.

In this case, the main controller 101 controls the movement mechanism 10D to change the relative position between the iris aperture 21 and the light source 10. By changing the relative position between the apertures 21A and 21B, which are formed in the iris aperture 21, and the light source 10, the light amount distribution of the light passing through the apertures 21A and 21B is changed. Further, the light amount distribution of the light, which passes through the apertures 21A and 21B formed in the iris aperture 21, at the aperture formed in the slit 22 is changed.

The main controller 101 can control the movement mechanism 10D based on the dioptric power of the subject's eye E as the state of the subject's eye E and the position of the slit 22 after the movement (or movement direction and movement amount of the slit 22 with reference to a reference position).

For example, the storage unit 102 stores second control information. In the second control information, at least one of the positions of the light source 10 and the orientations of the light source 10 are associated with the dioptric powers and the positions of the slit 22 after the movement (or the movement directions and movement amounts of the slit 22 with reference to the reference position) in advance. The main controller 101 identifies at least one of the position of the light source 10 and the orientation of the light source 10 corresponding to the dioptric power or the position of the slit 22 after the movement by referring to the second control information, and controls the movement mechanism 10D so that the light source 10 is arranged at the identified position or in the identified orientation.

In FIG. 9, the control for the optical scanner 30 includes control of the scan range (scan start position and scan end position) and the scan speed.

Control for the focus indicator optical system 36 includes control for the focus indicator light source, insertion control (removal control) of the above reflective rod. Here, the above reflective rod is used for coupling the optical path of the focus indicator light from the focus indicator optical system 36 with the optical path of the projection optical system 35.

The control for the focus indicator light source includes switching the focus indicator light source on and off, and changing the light amount of the light source. The insertion/removal control for the reflective rod includes the control of placing the reflective surface of the reflective rod on the optical path of the projection optical system 35 by controlling the moving mechanism not shown in the figure when the focus adjustment is performed, and the control of removing the reflective surface of the reflective rod from the optical path of the projection optical system 35 by controlling the moving mechanism not shown in the figure when the focus adjustment is not performed.

The control for the imaging optical system 40 includes control for a movement mechanism 47D (focus control). The movement mechanism 47D moves the focusing lens 47 in the optical axis direction of the imaging optical system 40. The main controller 101 can control the movement mechanism 47D based on an analysis result of the image acquired using the image sensor 51. For example, when performing focus adjustment, the main controller 101 controls the focus indicator optical system 36 as described above to project the focus indicator light onto the fundus Ef of the subject's eye E, identifies the two split indicator images depicted in the image acquired using the image sensor 51, and controls the movement mechanism 47D according to the Scheiner principle from the positional relationship between the identified two split indicator images. In some embodiments, without using the focus indicator optical system 36, the main controller 101 analyzes the image acquired using the image sensor 51 to identify whether or not it is in the focusing state, and controls the movement mechanism 47D according to the identification whether or not it is in the focusing state. Further, the main controller 101 can control the movement mechanism 47D based on a content of operation of the user using an operation unit 110 described below.

The control for the imaging device 50 includes a control for the image sensor 51 (rolling shutter control). The control for the image sensor 51 includes the reset control, the exposure control, the charge transfer control, and the output control. Further, time Tr required for the reset control, time (exposure time) Te required for the exposure control, time Tc required for the charge transfer control, and time Tout required for the output control, etc., can be changed.

Examples of the control for the data processor 200 include various kinds of image processing and various kinds of analysis processing on the light receiving results acquired from the image sensor 51. Examples of the image processing include noise removal processing on the light receiving results, brightness correction processing for easily identifying a predetermined site depicted in the light receiving image based on the light receiving results. Examples of the analysis processing include the identification processing of the split indicator images for the focus control described above, the identification processing of the control result for the focusing lens 47 (movement mechanism 47D) according to the Scheiner principle, and the identification processing of the focusing state. Examples of the identification processing of the control result for the focusing lens 47 include the identification processing of the position on the optical axis of the focusing lens 47. Examples of the identification processing of the focusing state include the identification processing of the control result for the focusing lens 47 based on the image contrast, and the identification processing of the control result for the focusing lens 47 based on the brightness in the brightest region in the image.

The data processor 200 can form the light receiving image corresponding to the arbitrary opening range based on the light receiving result(s) read out from the image sensor 51 using the rolling shutter method, under the control from the main controller 101 (controller 100). The data processor 200 can sequentially form light receiving light images corresponding to the opening ranges and can form an image of the subject's eye E from a plurality of formed light receiving images.

The data processor 200 includes a processor, and realizes the above functions by performing processing corresponding to the program(s) stored in the storage unit or the like.

In some embodiments, the light source 10 includes two or more light sources. In this case, each of the two or more light sources is provided corresponding to the two or more apertures formed in the iris aperture 21. The main controller 101 can change the at least one of a position of each light source and an orientation (orientation in the direction of maximum light amount distribution) of each light source, by controlling the movement mechanisms provided for each of the two or more light sources.

In some embodiments, at least one of the position of the optical element 24 and the orientation of the optical element 24 with respect to the aperture(s) formed in the iris aperture 21 can be changed. For example, the main controller 101 can change the at least one of the position of the optical element 24 and the orientation of the optical element 24 by controlling the movement mechanism that moves the optical element 24.

(Storage Unit 102)

The storage unit 102 stores various computer programs and data. The computer programs include an arithmetic program and a control program for controlling the ophthalmic apparatus 1.

In the present embodiment, the storage unit 102 stores the artifact information calculated in advance for each dioptric power. The artifact information is information for identifying at least one of the position, shape, and intensity of the black dot shadow depicted in the fundus image.

In some embodiments, the artifact information includes first artifact information and second artifact information. The first artifact information is shared for each ophthalmic apparatus type (ophthalmic apparatuses with substantially identical optical system configuration). The second artifact information is used for each ophthalmic apparatus. Examples of the first artifact information includes information for identifying the shape and intensity of the artifact(s) in the fundus image. Examples of the second artifact information includes information for identifying the position(s) of the artifact(s) in the fundus image. The first artifact information is assumed to be a parameter common to all ophthalmic apparatus types that acquire images of the subject's eye, and is preferably shared by a plurality of ophthalmic apparatuses of the same type. The second artifact information is assumed to be a parameter specific to the ophthalmic apparatus, and is preferably prepared for each ophthalmic apparatus.

The artifact information is calculated by performing an optical simulation in advance for each dioptric power, under a simulation condition corresponding to an optical condition in the optical system provided in the ophthalmic apparatus for acquiring fundus images of the subject's eye. In some embodiments, the artifact information is acquired by measuring in advance for each dioptric power, using the ophthalmic apparatus for acquiring fundus images of the subject's eye.

For example, the storage unit 102 stores 11 kinds of artifact information for each "2D(diopter)" between "−10D" and "+10D". In this case, two or more artifact information corresponding to the dioptric power of the subject's eye E can be identified, and interpolated artifact information obtained by interpolating the identified two or more artifact information can be identified as the artifact information associated with the dioptric power of the subject's eye E.

(Operation Unit 110)

The operation unit 110 includes an operation device or an input device. The operation unit 110 includes buttons and switches (e.g., operation handle, operation knob, etc.) and operation devices (e.g., mouse, keyboard, etc.) provided in the ophthalmic apparatus 1. In addition, the operation unit 110 may include any operation device or any input device, such as a trackball, a control panel, a switch, a button, a dial, etc.

(Display Unit 120)

The display unit 120 displays the image of the subject's eye E generated by data processor 200. The display unit 120 is configured to include a display device such as a flat panel display such as an LCD (Liquid Crystal Display). In addition, the display unit 120 may include various types of display devices such as a touch panel and the like provided in the housing of the ophthalmic apparatus 1.

It should be noted that the operation unit 110 and the display unit 120 do not need to be configured to be separate devices. For example, a device like a touch panel, which has a display function integrated with an operation function, can be used. In this case, the operation unit 110 includes the touch panel and a computer program. The content for the operation unit 110 is fed to the controller 100 as electrical signals. Moreover, operations and inputs of information may be performed using a graphical user interface (GUI) displayed on the display unit 120 and the operation unit 110. In some embodiments, the functions of the display unit 120 and the operation unit 110 are realized a touch screen.

(Example of Configuration of Data Processor 200)

The data processor 200 realizes the functions of the ophthalmic information processing apparatus according to the embodiments.

Figure 11:
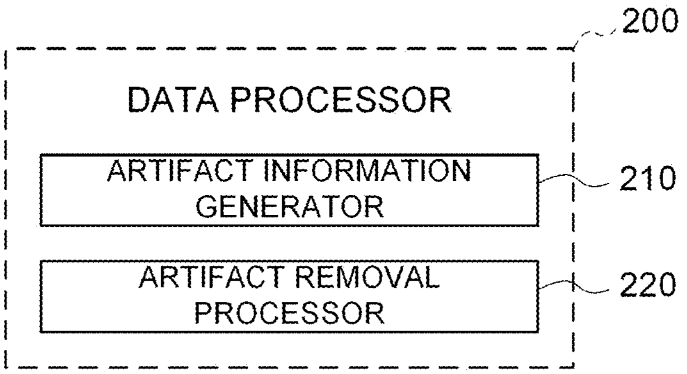
FIG. 11 is a schematic diagram illustrating an example of the configuration of the control system of the ophthalmic apparatus according to the embodiments.
Figure 12:
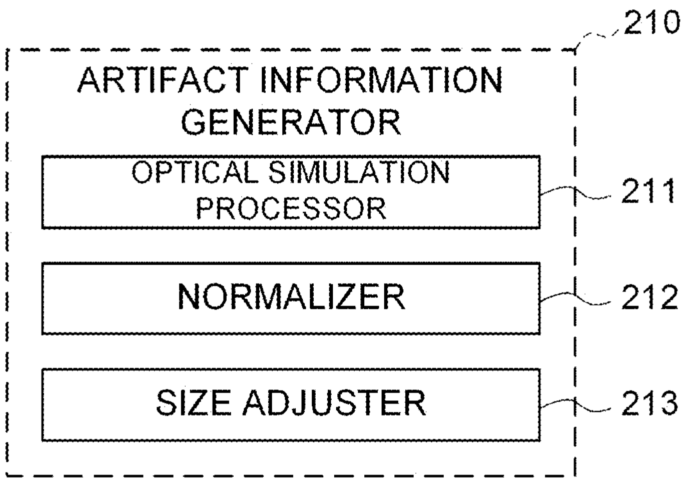
FIG. 12 is a schematic diagram illustrating an example of the configuration of the control system of the ophthalmic apparatus according to the embodiments.
Figure 13:
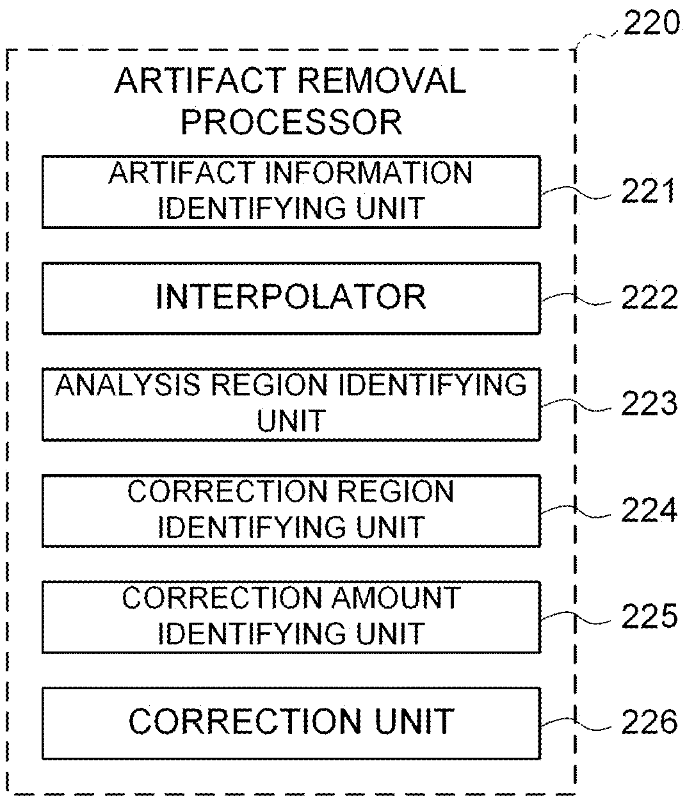
FIG. 13 is a schematic diagram illustrating an example of the configuration of the control system of the ophthalmic apparatus according to the embodiments.

FIGS. 11 to 13 show examples of the configuration of the data processor in FIG. 9. FIG. 11 shows a functional block diagram of the data processor 200 in FIG. 9. FIG. 12 shows a functional block diagram of an artifact information generator 210 in FIG. 11. FIG. 13 shows a functional block diagram of an artifact removal processor 220 in FIG. 11

As shown in FIG. 11, the data processor 200 includes the artifact information generator 210 and the artifact removal processor 220. The artifact information generator 210 generates the artifact information prior to the artifact removal processing performed by the artifact removal processor 220. The artifact removal processor 220 performs the artifact removal processing on the fundus image of the subject's eye E, using the artifact information generated in advance by the artifact information generator 210.

As shown in FIG. 12, the artifact information generator 210 includes an optical simulation processor 211, a normalizer 212, and a size adjuster 213.

The optical simulation processor 211 performs the optical simulation for each diopter under the simulation condition(s) to generate simulation data representing the position, the shape, and the intensity of the black dot image for each dioptric power. Here, the simulation condition simulates the optical condition(s) in the optical system (optical system 2 in FIG. 1A) of the ophthalmic apparatus 1 shown in FIG. 2. The optical system in the ophthalmic apparatus 1 includes the light source 10, the illumination optical system 20, the optical scanner 30, the projection optical system 35, the imaging optical system 40, and the imaging device 50.

The normalizer 212 normalizes the simulation data generated for each dioptric power. Examples of the normalization includes the processing of setting the maximum value of the intensity in each simulation data to "1".

The size adjuster 213 adjusts the size of the simulation data, which is normalized by the normalizer 212 and differs in the size of the black dot images depending on the dioptric power, so as to represent the black dot image on the light receiving surface (imaging surface) of the image sensor 51.

As shown in FIG. 13, the artifact removal processor 220 includes an artifact information identifying unit 221, an interpolator 222, an analysis region identifying unit 223, a correction region identifying unit 224, a correction amount identifying unit 225, and a correction unit 226.

The artifact information identifying unit 221 identifies one or more artifact information corresponding to the dioptric power of the subject's eye E from the artifact information for each dioptric power stored in advance in the storage unit 102. As described above, the dioptric power of the subject's eye E can be identified from the position on the optical axis of the focusing lens 47 when it is determined to be in the focusing state as the focus control result (or the control result for the actuator that moves the movement mechanism 47D), or from the measurement result in an external refractive power measurement apparatus.

When the artifact information associated with the dioptric power of the subject's eye E among the artifact information for each dioptric power is stored in the storage unit 102, the artifact information identifying unit 221 identifies the artifact information associated with the dioptric power of the subject's eye E. When the artifact information associated with the dioptric power of the subject's eye E among the artifact information for each dioptric power is not stored in the storage unit 102, the artifact information identifying unit 221 identifies two or more artifact information corresponding to two or more dioptric powers, in which the dioptric power of the subject's eye E is intermediate, among the artifact information for each dioptric power stored in the storage unit 102.

The artifact information identifying unit 221 may identify the artifact information associated with a second dioptric power that is calculated according to a predetermined approximation formula based on the artifact information associated with a first diopter stored in the storage unit 102.

When the artifact information associated with the dioptric power of the subject's eye is identified by the artifact information identifying unit 221, the interpolator 222 does not perform interpolation processing of the artifact information. When the two or more artifact information in which the dioptric power of the subject's eye E is intermediate, is identified by the artifact information identifying unit 221, the interpolator 222 performs interpolation processing on the identified two or more artifact information and generates interpolated artifact information associated with the dioptric power of the subject's eye E. Examples of the interpolation processing for two or more artifact information include weighted averaging, linear interpolation (interpolation or extrapolation), Lagrangian interpolation, and spline interpolation. For example, when the dioptric power of the subject's eye E is "−5D", the first artifact information corresponding to "−4D" and the second artifact information corresponding to "−6D" are read out from the storage unit 102. And, the interpolated artifact information obtained by performing weighted averaging on the readout first artifact information and second artifact information can be identified as the artifact information associated with "−5D".

The analysis region identifying unit 223 identifies an analysis region in the fundus image of the subject's eye E, based on the artifact information identified by the artifact information identifying unit 221 or the interpolated artifact information obtained by the interpolator 222. Specifically, the analysis region identifying unit 223 identifies the analysis region shifted from a reference position in the fundus image by a displacement of the reference position varying in accordance with the dioptric power of the subject's eye, based on the artifact information or the interpolated artifact information. In the present embodiment, examples of the reference position in the image include a position corresponding to the optical axis of the optical system in the ophthalmic apparatus. In other words, the analysis region identifying unit 223 can identify the analysis region shifted from a reference position in the image by the displacement of the reference position varying in accordance with the dioptric power of subject's eye E, based on the dioptric power of the subject's eye E and the optical condition(s) in the optical system of the ophthalmic apparatus 1.

The correction region identifying unit 224 identifies the correction region in the fundus image of the subject's eye E, based on the artifact information identified by the artifact information identifying unit 221 or the interpolated artifact information obtained by the interpolator 222. That is, the correction region identifying unit 224 can identify the correction region in the fundus image based on the dioptric power of the subject's eye E. When the analysis region has been identified by the analysis region identifying unit 223, the correction region identifying unit 224 identifies the correction region within the identified analysis region.

The correction amount identifying unit 225 identifies the correction amount of the luminance in the correction region identified by the correction region identifying unit 224, based on the artifact information identified by the artifact information identifying unit 221 or the interpolated artifact information obtained by the interpolator 222. That is, the correction amount identifying unit 225 can identify the correction amount of the luminance in the correction region identified in the fundus image, based on the dioptric power of the subject's eye E.

The correction unit 226 corrects the luminance in the correction region, based on the artifact information identified by the artifact information identifying unit 221 or the interpolated artifact information obtained by the interpolator 222. Specifically, the correction unit 226 corrects the luminance in the correction region identified by the correction region identifying unit 224, based on the correction amount identified by the correction amount identifying unit 225. That is, the correction unit 226 can correct the luminance in the correction region, based on the correction amount corresponding to the dioptric power of the subject's eye E.

When the artifact is the black dot shadow, the correction unit 226 corrects the luminance values of the pixels in the correction region so as to increase the luminance in the correction region. When the artifact is the center ghost, the correction unit 226 corrects the luminance values of the pixels in the correction region so as to decrease the luminance in the correction region.

(Other Configurations)

In some embodiments, the ophthalmic apparatus 1 further includes a fixation projection system. For example, an optical path of the fixation projection system is coupled with the optical path of the imaging optical system 40 in the configuration of the optical system shown in FIG. 2. The fixation projection system can present internal fixation targets or external fixation targets to the subject's eye E. In case of presenting the internal fixation target to the subject's eye E, the fixation projection system includes an LCD that displays the internal fixation target under the control from the controller 100, and projects a fixation light flux output from the LCD onto the fundus Ef of the subject's eye E. The LCD is configured to be capable of changing the display position of the fixation target on the screen of the LCD. By changing the display position of the fixation target on the screen of the LCD, the projected position of the fixation target on the fundus of the subject's eye E can be changed. The display position of the fixation target on the LCD can be designated using the operation unit 110 by the user.

In some embodiments, the ophthalmic apparatus 1 includes an alignment system. In some embodiments, the alignment system includes an XY alignment system and a Z alignment system. The XY alignment system is used for position matching between the optical system of the apparatus and the subject's eye E in a direction intersecting the optical axis of the optical system of the apparatus (objective lens 46). The Z alignment system is used for position matching between the optical system of the apparatus and the subject's eye E in a direction of the optical axis of the ophthalmic apparatus 1 (objective lens 46).

For example, the XY alignment system projects a bright spot (bright spot in the infrared region or near-infrared region) onto subject's eye E. The data processor 200 acquires an anterior segment image of the subject's eye E on which the bright spot is projected, and obtains the displacement between the bright spot image drawn on the acquired anterior segment image and an alignment reference position. The controller 100 relatively moves the optical system of the apparatus and the subject's eye E in the direction intersecting the direction of the optical axis so as to cancel the obtained displacement, using the movement mechanism.

For example, the Z alignment system projects alignment light in infrared region or the near-infrared region from a position away from the optical axis of the optical system of the apparatus, and receives the alignment light reflected on the anterior segment of the subject's eye E. The data processor 200 specifies a distance to the subject's eye E with respect to the optical system of the apparatus, from the light receiving position of the alignment light that changes in accordance with the distance to the subject's eye E with respect to the optical system of the apparatus. The controller 100 relatively moves the optical system of the apparatus and the subject's eye E in the direction of the optical axis using the movement mechanism (not shown) so that the specified distance becomes a predetermined working distance.

In some embodiments, the function of the alignment system is realized by two or more anterior segment cameras arranged at positions away from the optical axis of the optical system of the apparatus. For example, as disclosed in Japanese Unexamined Patent Application Publication No. 2013-248376, the data processor 200 analyzes data processor segment images of subject's eye E substantially simultaneously acquired using the two or more anterior segment cameras, and specifies a three-dimensional position of the subject's eye E using known trigonometry. The controller 100 controls the movement mechanism (not shown) to relatively move the optical system of the apparatus and the subject's eye E three-dimensionally so that the optical axis of the optical system of the apparatus substantially coincides with an axis of the subject's eye E and the distance of the optical system of the apparatus with respect to the subject's eye E is a predetermined working distance.

The movement mechanism 22D is an example of the "first movement mechanism" according to the embodiments. The movement mechanism 10D is an example of the "second movement mechanism" according to the embodiments. A movement mechanism (not shown) that changes at least one of the position of the optical element 24 and the orientation of the optical element 24 is an example of the "third movement mechanism" according to the embodiments. The data processor 200 is an example of the "ophthalmic information processing apparatus" according to the embodiments. The fundus image of the subject's eye is an example of the "image of the subject's eye" according to the embodiments. The correction region identifying unit 224 is an example of the "identifying unit" according to the embodiments.

[Operation]

Next, the operation of the ophthalmic apparatus 1 will be described.

In the present embodiment, first, the artifact information is generated prior to the removal processing of the artifact, and the artifact removal processing is performed on the fundus image using the generated artifact information.

Figure 14:
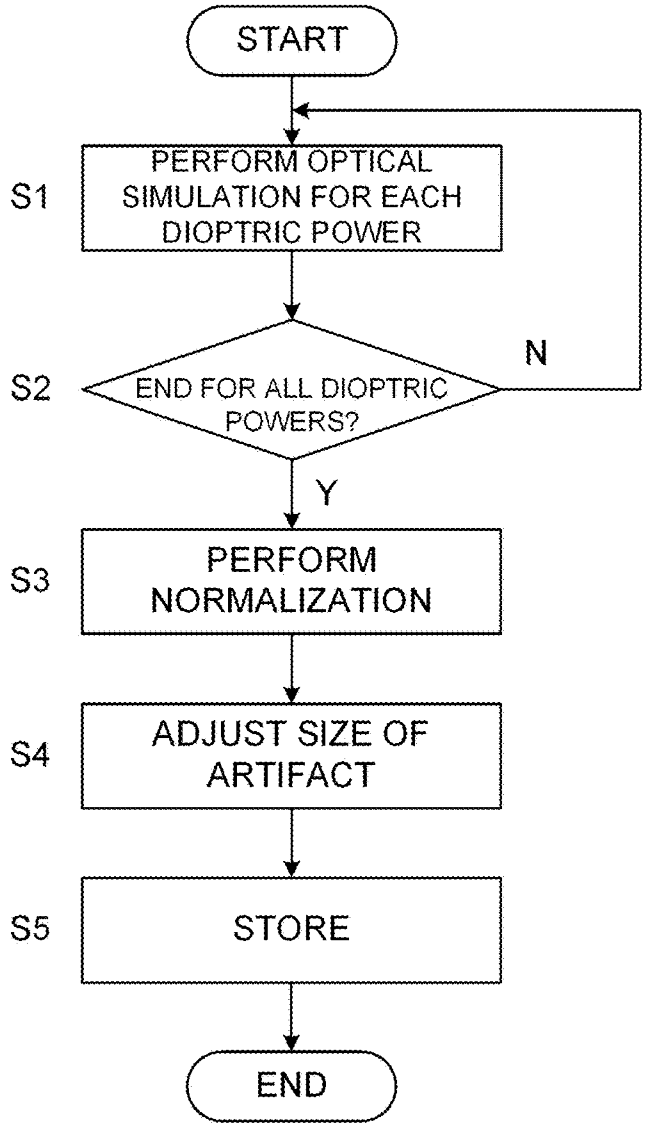
FIG. 14 is a flow chart of an example of an operation of the ophthalmic apparatus according to the embodiments.

FIG. 14 shows an example of a flow chart of the processing for generating the artifact information in the ophthalmic apparatus 1 according to the embodiments. The storage unit 102 stores computer program(s) for realizing the processing shown in FIG. 14. The main controller 101 operates according to the computer programs, and thereby the main controller 211 performs the processing shown in FIG. 14.

Figure 15A:
FIG. 15A is an explanatory diagram of an example of the operation of the ophthalmic apparatus according to the embodiments.
Figure 15B:
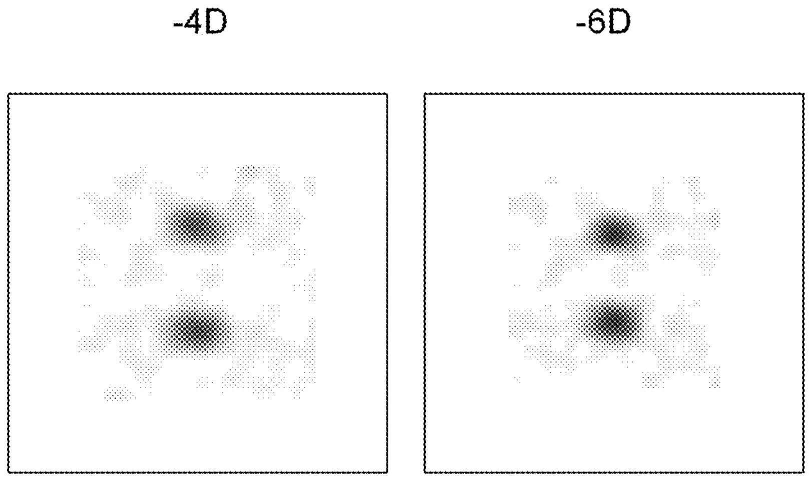
FIG. 15B is an explanatory diagram of an example of the operation of the ophthalmic apparatus according to the embodiments.

FIGS. 15A and 15B illustrate examples of the simulation data for describing the operation of each step in FIG. 14. FIG. 15A represents an example of the simulation data for describing the operations in steps S1 to S2 when the dioptric power is "−4D" and "−6D". FIG. represents an example of the simulation data for describing the operation in step S4 when the dioptric power is "−4D" and "−6D".

(S1: Perform Optical Simulation for Each Dioptric Power)

First, the main controller 101 controls the optical simulation processor 211 to perform the optical simulation using a known schematic eye having a predetermined dioptric power. This allows to acquire the simulation data representing the position, the shape, and the intensity of the black dot shadow for the predetermined dioptric power.

(S2: End for all Dioptric Powers?)

Subsequently, the main controller 101 determines whether or not the optical simulation has been performed for all dioptric powers within a predetermined dioptric power range.

When it is determined that the optical simulation has been performed for all dioptric powers (step S2: Y), the operation of the ophthalmic apparatus 1 proceeds to step S3. When it is determined that the optical simulation has not been performed for all dioptric powers (step S2: N), the operation of the ophthalmic apparatus 1 proceeds to step S1. When the operation proceeds to step S1, the optical simulation is performed for the next dioptric power at a predetermined dioptric power interval.

By repeating step S1 and step S2 within the predetermined dioptric power range at each predetermined dioptric power interval, the simulation data representing the position, the shape, and the intensity of the black dot shadow is obtained for each dioptric power. For example, 11 kinds of simulation data are obtained every "2D" from "−10D" to "+10D". For example, for the dioptric powers of "−4D" and "−6D", the simulation data as shown in FIG. 15A is obtained.

(S3: Perform Normalization)

Next, the main controller 101 controls the normalizer 212 to normalize the simulation data for each dioptric power obtained by repeating step S1 and step S2.

(S4: Adjust Size of Artifact)

Next, the main controller 101 controls the size adjuster 213 to perform size adjustment on the simulation data for each dioptric power normalized in step S3 so that the size of the black dot shadow becomes the size of the black dot image on the light receiving surface (imaging surface) of the image sensor 51. In some embodiments, the size adjuster 213 deletes data that does not fall within a predetermined region when it is judged that the data does not fall within the predetermined region as a result of the size adjustment. Or, the size adjuster 213 fills a predetermined region with the maximum value when it is judged to be smaller than the predetermined region as a result of the size adjustment.

For example, for the dioptric powers of "−4D" and "−6D", the simulation data as shown in FIG. 15B is obtained.

(S5: Store)

Next, the main controller 101 associates the simulation data for each dioptric power for which the size adjustment has been performed in step S4 with the dioptric power, and stores the simulation data in the storage unit 102.

This terminates the processing of generating the artifact information (END).

Next, the processing for acquiring the fundus images in the ophthalmic apparatus according to the embodiments will be described.

Figure 16:
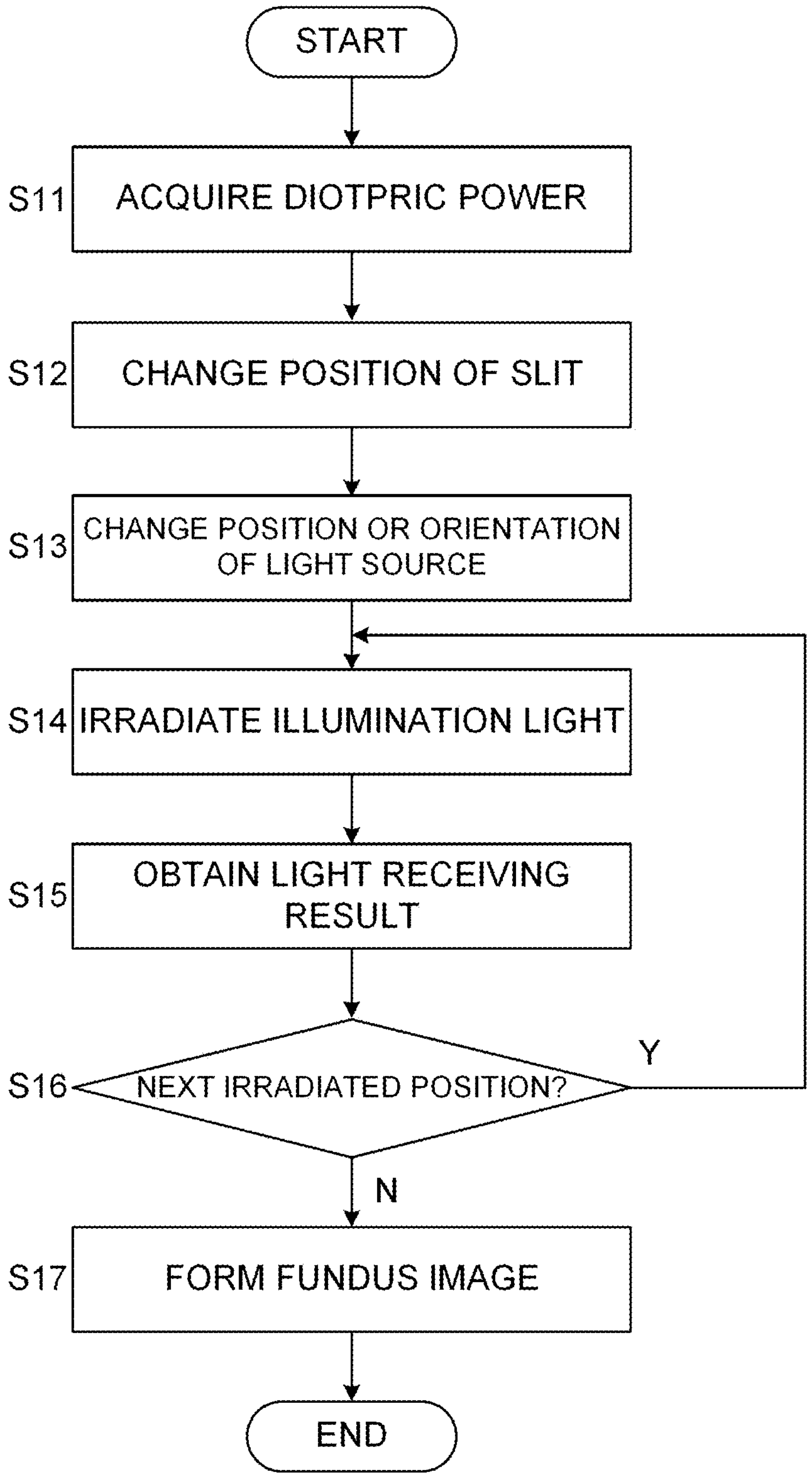
FIG. 16 is a flow chart of an example of the operation of the ophthalmic apparatus according to the embodiments.

FIG. 16 shows an example of a flow chart of the processing for acquire the fundus images in the ophthalmic apparatus 1 according to the embodiments. The storage unit 102 stores computer program(s) for realizing the processing shown in FIG. 16. The main controller 101 operates according to the computer programs, and thereby the main controller 101 performs the processing shown in FIG. 16.

Here, it is assumed that the alignment of the optical system of the apparatus with relative to the subject's eye E using the alignment system (not shown) is completed, that the fixation target is projected onto the fundus of the subject's eye E to guide the subject's eye E to a desired fixation position using the fixation projection system (not shown), and that the optical system is set to the focusing state by focus control using the focus indicator optical system 36 and the focusing lens 47.

(S11: Acquire Dioptric Power)

First, the main controller 101 acquires the dioptric power. For example, the main controller 101 identifies the dioptric power from the position on the axis of the focusing lens 47 having been set to the focusing state (or the control result for the actuator that moves the movement mechanism 47D). The main controller 101 may acquire the dioptric power of the subject's eye E from the external ophthalmic measurement apparatus or the electronic medical record.

(S12: Change Position of Slit)

Next, the main controller 101 changes the position of the slit 22 on the optical axis of the illumination optical system 20 in accordance with the dioptric power of the subject's eye E acquired in step S11.

Specifically, the main controller 101 specifies the position of the slit 22 corresponding to the dioptric power by referring to the first control information stored in the storage unit 102, and controls the movement mechanism 22D so as to arrange the slit 22 at the identified position.

(S13: Change Position or Orientation of Light Source)

Subsequently, the main controller 101 changes at least one of the position of the light source 10 and the orientation of the light source 10 in accordance with the new position of the slit 22 whose position on the optical axis has been changed in step S12.

Specifically, the main controller 101 identifies at least one of the position and the orientation of the light source 10 that corresponds to the dioptric power or the position of the slit 22 after the movement, by referring to the second control information stored in the storage unit 102. And then, the main controller 101 controls the movement mechanism 10D so that the light source 10 is arranged at the specified position or in the specified orientation.

(S14: Irradiate Illumination Light)

Next, the main controller 101 controls the illumination optical system 20 to generate the slit-shaped illumination light, and to start the deflection control of the optical scanner 30 to start irradiating the illumination light onto a desired irradiated region on the fundus Ef. When the irradiation of the illumination light is started, the slit-shaped illumination light is sequentially irradiated within the desired irradiated range as described above.

(S15: Obtain Light Receiving Result)

The main controller 101 acquires the light receiving result(s) of the pixels in the opening range of the image sensor 51 corresponding to the irradiated range of the illumination light on the fundus Ef performed in step S14, as described above.

(S16: Next Irradiated Position?)

The main controller 101 determines whether or not the next irradiated position is to be irradiated with the illumination light. The main controller 101 can determine whether or not the next irradiated position is to be irradiated with the illumination light, by determining whether or not the irradiated range of the illumination light that is moved sequentially has covered a predetermined imaging range of the fundus Ef.

When it is determined that the next irradiated position is to be irradiated with the illumination light (step S16: Y), the operation of the ophthalmic apparatus 1 proceeds to step S14. When it is determined that the next irradiated position is not to be irradiated with the illumination light (step S16: N), the operation of the ophthalmic apparatus 1 proceeds to step S17.

(S17: Form Fundus Image)

In step S16, when it is determined that the next irradiated position is not to be irradiated with the illumination light (step S16: N), the main controller 101 controls the data processor 200 to form the image of the subject's eye E from the light receiving results acquired repeatedly while changing the irradiated range of the illumination light in step S15.

For example, the data processor 200 syntheses a plurality of light receiving results with different irradiated ranges (opening ranges on the light receiving surface SR of the image sensor 51) of the illumination light for the number of times repeating the process in steps S14 to S16, based on the order of the movement of the irradiated range. Thereby, the fundus image of the fundus Ef for one frame is formed.

In some embodiments, in step S14, the illumination light is irradiated on the irradiated range set so as to have an overlapping region with the adjacent irradiated range. Thereby, in step S17, the fundus image for one frame is formed by synthesizing the overlapping regions so as to overlap with each other.

This terminates the processing of acquiring the fundus image in the ophthalmic apparatus 1 (END).

Subsequently, the artifact removal processing for the fundus image formed according to the flow shown in FIG. 16, using the artifact information for each dioptric power generated according to the flow shown in FIG. 14, will be described.

Figure 17:
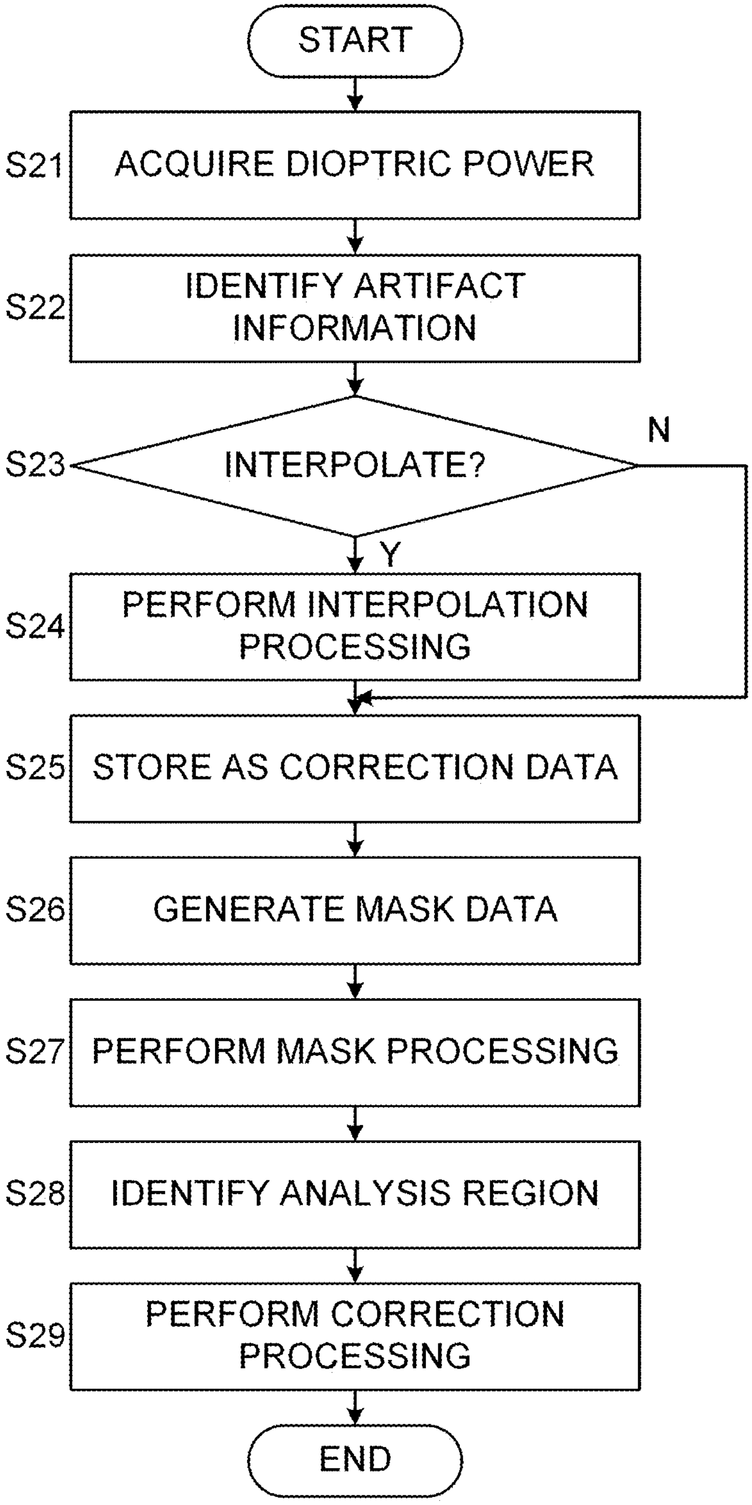
FIG. 17 is a flow chart of an example of the operation of the ophthalmic apparatus according to the embodiments.

FIG. 17 shows an example of a flow chart of the artifact removal processing for the fundus image in the ophthalmic apparatus 1 according to the embodiments. The storage unit 102 stores computer program(s) for realizing the processing shown in FIG. 17. The main controller 101 operates according to the computer programs, and thereby the main controller 101 performs the processing shown in FIG. 17.

(S21: Acquire Dioptric Power)

First, the main controller 101 acquires the dioptric power. The main controller 101 can acquire the dioptric power in the same way as in step S11.

(S22: Identify Artifact Information)

Next, the main controller 101 controls the artifact information identifying unit 221 to identify the artifact information corresponding to the dioptric power of the subject's eye E acquired in step S21 among the artifact information for each dioptric power generated according to the flow shown in FIG. 14.

The artifact information identifying unit 221 identifies the artifact information associated with the dioptric power acquired in step S21 or two or more artifact information associated with a dioptric power in which the dioptric power acquired in step S21 is intermediate, among the artifact information for each dioptric power stored in the storage unit 102, as described above.

(S23: Interpolate?)

Next, the main controller 101 determines from the result of the identification processing of the artifact information in step S22 whether or not to perform interpolation processing of the artifact information.

For example, when the artifact information associated with the dioptric power acquired in step S21 is stored in the storage unit 102, the main controller 101 can determine that the interpolation processing of the artifact information is not to be performed. In contrast, when the artifact information associated with the dioptric power acquired in step S21 is not stored in the storage unit 102, the main controller 101 can determine that the interpolation processing of the artifact information is to be performed.

When it is determined in step S23 that the interpolation processing of the artifact information is to be performed (step S23: Y), the operation of the ophthalmic apparatus 1 proceeds to step S24. On the other hand, when it is determined in step S23 that the interpolation processing of the artifact information is not to be performed (step S23: N), the operation of the ophthalmic apparatus 1 proceeds to step S25.

(S24: Perform Interpolation Processing)

When it is determined in step S23 that the interpolation processing of the artifact information is to be performed (step S23: Y), the main controller 101 controls the interpolator 222 to perform interpolation processing on the two or more artifact information identified in step S22 and to acquire the interpolated artifact information.

Figure 18A:
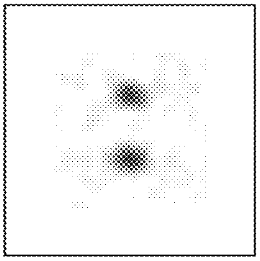
FIG. 18A is an explanatory diagram of an example of the operation of the ophthalmic apparatus according to the embodiments.

For example, for the dioptric power of "−5D", the interpolator 222 performs weighted averaging on the artifact information associated with "−4D" and the artifact information associated with "−6D" as shown in FIG. 15B to acquire the interpolated artifact information associated with "−5D". The interpolator 222 acquires the generated interpolated artifact information as correction data (correction magnification data) as shown in FIG. 18A.

(S25: Store as Correction Data)

Subsequent to step S24, or when it is determined in step S23 that the interpolation processing of the artifact information is not to be performed (step S23: N), the main controller 101 stores the interpolated artifact information acquired in step S24 or the artifact information associated with the dioptric power identified in step S22 in the storage unit 102 or a storage device not shown in figure, as the correction data.

(S26: Generate Mask Data)

Next, the main controller 101 controls the correction region identifying unit 224 to generate mask data from the correction data stored in step S25.

Figure 18B:
FIG. 18B is an explanatory diagram of an example of the operation of the ophthalmic apparatus according to the embodiments.
Figure 18C:
FIG. 18C is an explanatory diagram of an example of the operation of the ophthalmic apparatus according to the embodiments.

For example, the correction region identifying unit 224 binarizes the correction data stored in step S25, identifies connected regions in the correction data by performing a labeling processing on the binarized correction data, and deletes the connected regions less than a predetermined size (FIG. 18B). Then, the correction region identifying unit 224 applies the expansion processing to the correction data having the connected region(s) equal to or greater than the predetermined size to generate the mask data with a shape corresponding to the shape of the black dot shadow to be corrected shown in FIG. 18C.

(S27: Perform Mask Processing)

Figure 18D:
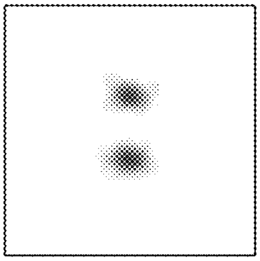
FIG. 18D is an explanatory diagram of an example of the operation of the ophthalmic apparatus according to the embodiments.

Subsequently, the main controller 101 performs the mask processing using the generated mask data generated in step S26 on the correction data stored in step S25 to generate final correction data shown in FIG. 18D.

(S28: Identify Analysis Region)

Next, the main controller 101 controls the analysis region identifying unit 223 to identify the analysis region in the fundus image from the interpolated artifact information acquired in step S24 or the artifact information associated with the dioptric power identified in step S22.

The analysis region identifying unit 223 identifies the analysis region including the position of the black dot shadow in the fundus image specific to the ophthalmic apparatus, from the interpolated artifact information or the artifact information. This allows to remove the artifact with high precision, while suppressing the effect caused by the displacement of the position of the artifact such as black dot shadow by shifting in the incident direction of the light passing near the edge of the aperture due to errors in the optical arrangement specific to the apparatus, such as the iris aperture 21, the slit 22, and the perforated mirror 45.

For example, the size (size in the horizontal direction and size in the vertical direction) of the analysis region identified by the analysis region identifying unit 223 is equivalent to the size of the correction data.

(S29: Perform Correction Processing)

Subsequently, the main controller 101 controls the correction amount identifying unit 225 to identify the correction amount of the correction region from the final correction data generated in step S27. After that, the main controller 101 controls the correction unit 226 to correct the luminance values of pixels in the correction area having a shape corresponding to the shape of the mask data in the analysis region identified in step S28 with the identified correction amount.

In the present embodiment, the correction unit 226 corrects the luminance values of pixels in the region corresponding to the mask data so that the luminance becomes higher. It should be noted that when the artifact is the center ghost, the correction unit 226 corrects the luminance values of the pixels in the region so that the luminance becomes lower.

This terminates the artifact removal processing for the fundus image (END).

Figure 19:
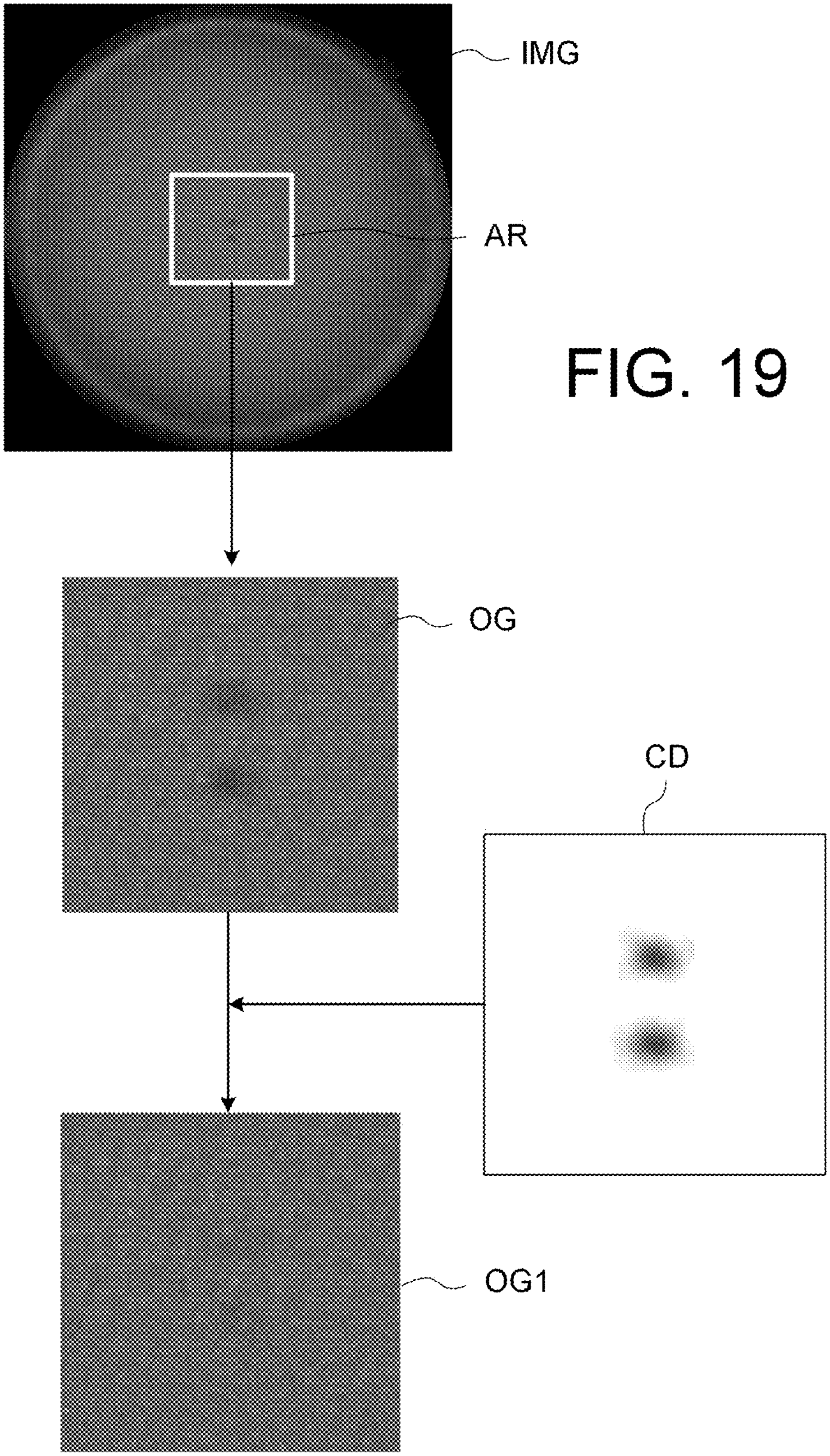
FIG. 19 is an explanatory diagram of an example of the operation of the ophthalmic apparatus according to the embodiments.

FIG. 19 shows a diagram explaining the operation of the removal processing of the black dot shadow in the ophthalmic apparatus 1 according to the embodiments.

As described above, the ophthalmic apparatus 1 generates the artifact information for each dioptric power according to the flow shown in FIG. 14, in advance. When the ophthalmic apparatus 1 acquires the fundus image IMG in the focusing state according to the flow shown in FIG. 16, the ophthalmic apparatus 1 identifies the dioptric power of the subject's eye E from the position of the focusing lens 47 in the focusing state, and identifies the artifact information (interpolated artifact information) corresponding to the dioptric power of the subject's eye E from the artifact information for each dioptric power.

Next, the ophthalmic apparatus 1 identifies the region AR to be analyzed in the fundus image IMG, and also identifies the correction data (final correction data) CD corresponding to the dioptric power of the subject's eye E and the correction region having the shape of the black dot shadow corresponding to the dioptric power of the subject's eye E in the analysis region AR. By correcting the luminance values of pixels in the correction region using the correction data CD, the ophthalmic apparatus 1 removes the black dot shadow in the correction region within the image region OG that varies in accordance with the dioptric power of the subject's eye E in the fundus image IMG, and acquires image region OG1 from which the black dot shadow has been removed.

Modification Example

The case has been described where the fundus Ef is illuminated while the optical scanner deflects the slit-shaped light in the ophthalmic apparatus 1 according to the embodiments. However, the configuration of the ophthalmic apparatus according to the embodiments is not limited thereto. For example, the ophthalmic apparatus 1 according to the embodiments may have the configuration of a so-called fundus camera.

In the following, the ophthalmic apparatus according to a modification example of the embodiments will be described focusing on differences from the ophthalmic apparatus according to the embodiments.

Figure 20:
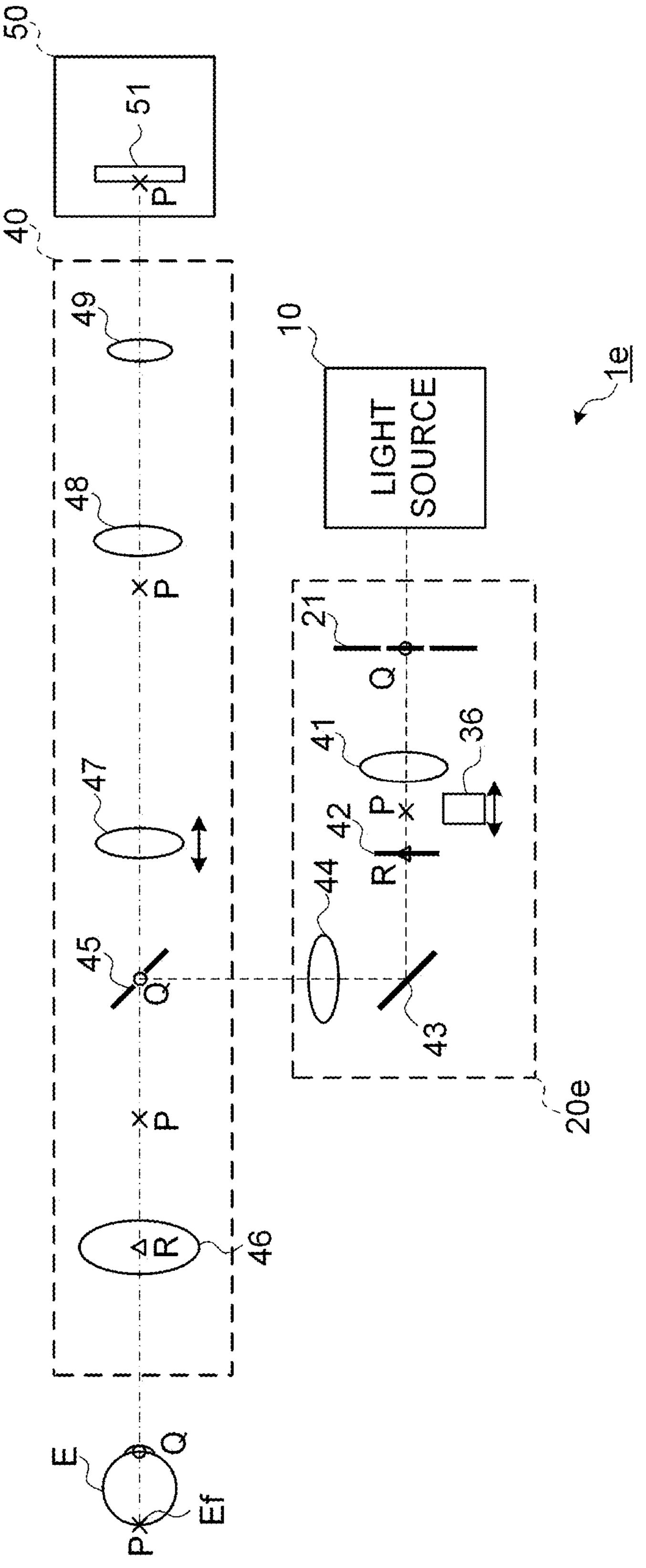
FIG. 20 is a schematic diagram illustrating an example of a configuration of an optical system of the ophthalmic apparatus according to a modification example of the embodiments.

FIG. 20 illustrates an example of a configuration of an optical system of the ophthalmic apparatus according to the modification example of the embodiments. In FIG. 20, the same parts as in FIG. 2 are shown by the same symbols and their descriptions will be omitted in an appropriate manner.

The configuration of the ophthalmic apparatus 1*e* according to the modification example of the embodiments differs from that of the ophthalmic apparatus 1 according to the embodiment in that an illumination optical system 20*e* is provided instead of the illumination optical system 20 and the projection optical system 35.

The illumination optical system 20*e* includes an optical element in the projection optical system 35 and the iris aperture 21 in the illumination optical system 20.

Such an ophthalmic apparatus 1*e* can include a control system similar to the control system of the ophthalmic apparatus 1 according to the embodiment, except that the slit-shaped light deflection control is omitted.

[Actions]

The ophthalmic information processing apparatus, the ophthalmic apparatus, the ophthalmic information processing method, and the program according to the embodiments will be described.

The first aspect of some embodiments is an ophthalmic information processing apparatus (400, 400*d*, data processor 200) for removing an artifact (black dot shadow, center ghost) of an image (fundus image) of a subject's eye (E) obtained using an ophthalmic apparatus (1, 1*a*, 1*b*, 1*c*, 1*e*). The ophthalmic information processing apparatus includes an identifying unit (correction region identifying unit 224) and a correction unit (226). The identifying unit is configured to identify a correction region in the image based on a dioptric power (refractive power) of the subject's eye. The correction unit is configured to correct a luminance in the correction region identified by the identifying unit, based on a correction amount corresponding to the dioptric power of the subject's eye.

According to such an aspect, artifacts in the image of the subject's eye that vary in accordance with the dioptric power of the subject's eye can be removed with a simple processing.

In the second aspect of some embodiments, in the ophthalmic information processing apparatus in the first aspect, the identifying unit is configured to identify the correction region based on artifact information for each dioptric power, the artifact information being obtained by calculating a position, a shape, and an intensity of the artifact in the image in advance. The correction unit is configured to correct the luminance in the correction region, based on the artifact information for each dioptric power.

According to such an aspect, even when the optical conditions vary depending on the ophthalmic apparatus, the artifact(s) in the image of the subject's eye that change in accordance with the dioptric power of the subject's eye can be removed with a simple processing.

In the third aspect of some embodiments, the ophthalmic information processing apparatus in the second aspect further includes an interpolator (222) configured to interpolate artifact information of two or more dioptric powers based on the dioptric power of the subject's eye, the artifact information of two or more dioptric power being identified based on the dioptric power of the subject's eye. The identifying unit is configured to identify the correction region based on interpolated artifact information obtained by the interpolator. The correction unit is configured to correct the luminance in the correction region based on the interpolated artifact information.

According to such an aspect, even when there is no artifact information associated with the dioptric power of the subject's eye, by identifying interpolated artifact information obtained by interpolating the artifact information associated with the existing dioptric power, the correction region can be identified based on the identified interpolated artifact information and can be removed the artifact.

In the fourth aspect of some embodiments, in the ophthalmic information processing apparatus in any one of the first aspect to the third aspect, the artifact is a black dot shadow formed by a black dot (42) provided in the ophthalmic apparatus. The correction unit is configured to increase the luminance in the correction region.

According to such an aspect, the black dot shadows, which vary in accordance with the dioptric power of the subject's eye and are depicted in the image of the subject's eye, can be removed with a simple processing, or the effects of the black dot shadows can be significantly reduced.

In the fifth aspect of some embodiments, in the ophthalmic information processing apparatus in any one of the first aspect to the third aspect, the artifact is a center ghost formed by an objective lens (46) provided in the ophthalmic apparatus. The correction unit is configured to decrease the luminance in the correction region.

According to such an aspect, the center ghosts, which vary in accordance with the dioptric power of the subject's eye and are depicted in the image of the subject's eye, can be removed with a simple processing, or the effects of the center ghosts can be significantly reduced.

In the sixth aspect of some embodiments, the ophthalmic information processing apparatus in any one of the first aspect to the third aspect further includes an analysis region identifying unit (223) and a correction amount identifying unit (225). The analysis region identifying unit is configured to identify an analysis region shifted from a reference position (position corresponding to the optical axis, center position of the image) in the image by a displacement of the reference position varying in accordance with the dioptric power of the subject's eye, based on the dioptric power of the subject's eye and an optical condition in an optical system (2, 2*b*, light source 10, illumination optical systems 20, 20*e*, optical scanner 30, imaging optical system 40, and imaging device 50) of the ophthalmic apparatus. The correction amount identifying unit is configured to identify the correction amount in the image based on the dioptric power of the subject's eye. The correction unit is configured to correct the luminance in the correction region based on the correction amount, the correction region being identified in the analysis region by the identifying unit, the analysis region being identified by the analysis region identifying unit.

According to such an aspect, the artifacts can be removed with high precision, while suppressing the effect caused by the displacement of the position of the artifact by shifting in the incident direction of the light passing near the edge of the diaphragm or the aperture due to errors in the optical arrangement specific to the apparatus in the optical element (diaphragm, aperture) arranged on the optical path of illumination light or imaging light.

In the seventh aspect of some embodiments, the ophthalmic information processing apparatus in any one of the first aspect to the third aspect includes a focusing lens (47) that is movable along an optical axis of an optical system. The identifying unit is configured to identify the correction region corresponding to the dioptric power of the subject's eye based on a position on the optical axis of the focusing lens. The correction unit is configured to correct the luminance in the correction region based on the position on the optical axis of the focusing lens.

According to such an aspect, the dioptric power of the subject's eye is identified based on the position on the optical axis of the focusing lens. Thereby, the artifacts in the image of the subject's eye, which vary in accordance with the dioptric power of the subject's eye, can be removed with a simple processing.

The eighth aspect of some embodiments is an ophthalmic apparatus (1, 1*a*, 1*b*, 1*c*, 1*e*) including: an illumination optical system (20, 20*e*) configured to irradiate illumination light onto the subject's eye; an imaging optical system (40) configured to acquire an image of the subject's eye by receiving returning of the illumination light from the subject's eye; and an ophthalmic information processing apparatus (400, 400*d*, data processor 200) in any one of the first aspect to the third aspect configured to remove an artifact of the image acquired by the imaging optical system.

According to such an aspect, the ophthalmic apparatus capable of removing artifact(s) in the image of the subject's eye that vary in accordance with the dioptric power of the subject's eye with a simple processing can be provided.

The ninth aspect of some embodiments is an ophthalmic information processing method of removing an artifact (black dot shadow, center ghost) of an image (fundus image) of a subject's eye (E) obtained using an ophthalmic apparatus (1, 1*a*, 1*b*, 1*c*, 1*e*). The ophthalmic information processing method includes an identifying step and a correction step. The identifying step is performed to identify a correction region in the image based on a dioptric power (refractive power) of the subject's eye. The correction step is performed to correct a luminance in the correction region identified in the identifying step, based on a correction amount corresponding to the dioptric power of the subject's eye.

According to such an aspect, artifacts in the image of the subject's eye that vary in accordance with the dioptric power of the subject's eye can be removed with a simple processing.

In the tenth aspect of some embodiments, in the ophthalmic information processing method in the ninth aspect, the identifying step is performed to identify the correction region based on artifact information for each dioptric power, the artifact information being obtained by calculating a position, a shape, and an intensity of the artifact in the image in advance. The correction step is performed to correct the luminance in the correction region, based on the artifact information for each dioptric power.

According to such an aspect, even when the optical conditions vary depending on the ophthalmic apparatus, the artifact(s) in the image of the subject's eye that change in accordance with the dioptric power of the subject's eye can be removed with a simple processing.

In the eleventh aspect of some embodiments, the ophthalmic information processing method in the tenth aspect further includes an interpolation step of interpolating artifact information of two or more dioptric powers based on the dioptric power of the subject's eye, the artifact information of two or more dioptric power being identified based on the dioptric power of the subject's eye. The identifying step is performed to identify the correction region based on interpolated artifact information obtained in the interpolation step. The correction step is performed to correct the luminance in the correction region based on the interpolated artifact information.

According to such an aspect, even when there is no artifact information associated with the dioptric power of the subject's eye, by identifying interpolated artifact information obtained by interpolating the artifact information associated with the existing dioptric power, the correction region can be identified based on the identified interpolated artifact information and can be removed the artifact.

In the twelfth aspect of some embodiments, in the ophthalmic information processing method in any one of the ninth aspect to the eleventh aspect, the artifact is a black dot (42) shadow formed by a black dot provided in the ophthalmic apparatus. The correction step is performed to increase the luminance in the correction region.

According to such an aspect, the black dot shadows, which vary in accordance with the dioptric power of the subject's eye and are depicted in the image of the subject's eye, can be removed with a simple processing, or the effects of the black dot shadows can be significantly reduced.

In the thirteenth aspect of some embodiments, in the ophthalmic information processing method in any one of the ninth aspect to the eleventh aspect, the artifact is a center ghost formed by an objective lens (46) provided in the ophthalmic apparatus. The correction step is performed to decrease the luminance in the correction region.

According to such an aspect, the center ghosts, which vary in accordance with the dioptric power of the subject's eye and are depicted in the image of the subject's eye, can be removed with a simple processing, or the effects of the center ghosts can be significantly reduced.

In the fourteenth aspect of some embodiments, the ophthalmic information processing method in any one of the ninth aspect to the eleventh aspect further includes an analysis region identifying step and a correction amount identifying step. The analysis region identifying step is performed to identify an analysis region shifted from a reference position (position corresponding to the optical axis, center position of the image) in the image by a displacement of the reference position varying in accordance with the dioptric power of the subject's eye, based on the dioptric power of the subject's eye and an optical condition in an optical system (2, 2*b*, light source 10, illumination optical systems 20 and 20*e*, optical scanner 30, imaging optical system 40, and imaging device 50) of the ophthalmic apparatus. The correction amount identifying step is performed to identify the correction amount in the image based on the dioptric power of the subject's eye. The correction step is performed to correct the luminance in the correction region based on the correction amount, the correction region being identified in the analysis region in the identifying step, the analysis region being identified in the analysis region identifying step.

According to such an aspect, the artifacts can be removed with high precision, while suppressing the effect caused by the displacement of the position of the artifact by shifting in the incident direction of the light passing near the edge of the diaphragm or the aperture due to errors in the optical arrangement specific to the apparatus in the optical element (diaphragm, aperture) arranged on the optical path of illumination light or imaging light.

In the fifteenth aspect of some embodiments, the ophthalmic information processing method in any one of the ninth aspect to the eleventh aspect further includes a focusing lens (47) that is movable along an optical axis of an optical system. The identifying step is performed to identify the correction region corresponding to the dioptric power of the subject's eye based on a position on the optical axis of the focusing lens. The correction step is performed to correct the luminance in the correction region based on the position on the optical axis of the focusing lens.

According to such an aspect, the dioptric power of the subject's eye is identified based on the position on the optical axis of the focusing lens. Thereby, the artifacts in the image of the subject's eye, which vary in accordance with the dioptric power of the subject's eye, can be removed with a simple processing.

The sixteenth aspect of some embodiments is a program of causing a computer to execute each step of the ophthalmic information processing method in any one of the ninth aspect to the eleventh aspect.

According to such an aspect, the program capable of removing artifact(s) in the image of the subject's eye that vary in accordance with the dioptric power of the subject's eye with a simple processing can be provided.

The embodiments or the modification example thereof described above are merely examples for carrying out the present invention. Those who intend to implement the present invention can apply any modification, omission, addition, or the like within the scope of the gist of the present invention.

In the above embodiments, the ophthalmic apparatus may have arbitrary functions adaptable in the field of ophthalmology. Examples of such functions include an axial length measurement function, a tonometry function, an optical coherence tomography (OCT) function, an ultrasonic inspection, and the like. It should be noted that the axial length measurement function is realized by the OCT, etc. Further, the axial length measurement function may be used to measure the axial length of the subject's eye by projecting light onto the subject's eye and detecting the returning light from the fundus while adjusting the position of the optical system in the Z direction (front-back direction) relative to the subject's eye. The intraocular pressure measurement function is realized by the tonometer, etc. The OCT function is realized by the OCT apparatus, etc. The ultrasonic inspection function is realized by the ultrasonic diagnosis apparatus, etc. Further, the present invention can also be applied to an apparatus (multifunctional apparatus) having two or more of such functions.

In some embodiments, a program for causing a computer to execute the ophthalmic information processing method described above is provided. Such a program can be stored in any non-transitory computer-readable recording medium. Examples of the recording medium include a semiconductor memory, an optical disk, a magneto-optical disk (CD-ROM, DVD-RAM, DVD-ROM, MO, etc.), a magnetic storage medium (hard disk, floppy (registered trade mark) disk, ZIP, etc.), and the like. The computer program may be transmitted and received through a network such as the Internet, LAN, etc.

The invention has been described in detail with particular reference to preferred embodiments thereof and examples, but it will be understood that variations and modifications can be effected within the spirit and scope of the invention covered by the claims which may include the phrase "at least one of A, B and C" as an alternative expression that means one or more of A, B and C may be used, contrary to the holding in Superguide v. DIRECTV, 69 USPQ2d 1865 (Fed. Cir. 2004).

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An ophthalmic information processing apparatus comprising:

processing circuitry configured as an identifying unit to identify a correction region in an image of a subject's eye, the image being obtained using an ophthalmic apparatus, based on a dioptric power of the subject's eye; and the processing circuitry further configured as a correction unit to correct a luminance in the correction region identified by the identifying unit to remove an artifact of the image, based on a correction amount corresponding to the dioptric power of the subject's eye, wherein the identifying unit is configured to identify the correction region based on artifact information for each dioptric power, the artifact information being obtained by performing an optical simulation in advance for each dioptric power, under a simulation condition corresponding to an optical condition in an optical system provided in the ophthalmic apparatus for obtaining the image, and calculating a position, a shape, and an intensity of the artifact in the image in advance, the correction unit is configured to correct the luminance in the correction region, based on the artifact information for each dioptric power, the artifact information includes first artifact information and second artifact information, the first artifact information being information that is shared in common between a plurality of ophthalmic apparatuses having a same model type and same optical system configuration, the second artifact information being information that is specific to the ophthalmic apparatus.

2. The ophthalmic information processing apparatus of claim 1, wherein the processing circuitry is further configured as an interpolator configured to interpolate artifact information of two or more dioptric powers based on the dioptric power of the subject's eye, the artifact information of two or more dioptric power being identified based on the dioptric power of the subject's eye, wherein the identifying unit is configured to identify the correction region based on interpolated artifact information obtained by the interpolator, and the correction unit is configured to correct the luminance in the correction region based on the interpolated artifact information.

3. The ophthalmic information processing apparatus of claim 1, wherein the artifact is a black dot shadow formed by a black dot provided in the ophthalmic apparatus, and the correction unit is configured to increase the luminance in the correction region.

4. The ophthalmic information processing apparatus of claim 1, wherein the artifact is a center ghost formed by an objective lens provided in the ophthalmic apparatus, and the correction unit is configured to decrease the luminance in the correction region.

5. The ophthalmic information processing apparatus of claim 1, wherein:

the processing circuitry is further configured as an analysis region identifying unit configured to identify an analysis region shifted from a reference position in the image by a displacement of the reference position varying in accordance with the dioptric power of the subject's eye, based on the dioptric power of the subject's eye and an optical condition in an optical system of the ophthalmic apparatus; and the processing circuitry is further configured as a correction amount identifying unit configured to identify the correction amount in the image based on the dioptric power of the subject's eye, wherein the correction unit is configured to correct the luminance in the correction region based on the correction amount, the correction region being identified in the analysis region by the identifying unit, the analysis region being identified by the analysis region identifying unit.

6. The ophthalmic information processing apparatus of claim 1, wherein the ophthalmic apparatus includes a focusing lens that is movable along an optical axis of the optical system, the identifying unit is configured to identify the correction region corresponding to the dioptric power of the subject's eye based on a position on the optical axis of the focusing lens, and the correction unit is configured to correct the luminance in the correction region based on the position on the optical axis of the focusing lens.

7. An ophthalmic apparatus, comprising:

an illumination optical system configured to irradiate illumination light onto the subject's eye;

an imaging optical system configured to acquire an image of the subject's eye by receiving returning of the illumination light from the subject's eye; and an ophthalmic information processing apparatus configured to remove an artifact of the image acquired by the imaging optical system, wherein the ophthalmic information processing apparatus comprising:

an identifying circuit configured to identify a correction region in the image of the subject's eye, the image being obtained using the ophthalmic apparatus, based on a dioptric power of the subject's eye; and a correction circuit configured to correct a luminance in the correction region identified by the identifying circuit to remove the artifact of the image, based on a correction amount corresponding to the dioptric power of the subject's eye, wherein the identifying circuit is configured to identify the correction region based on artifact information for each dioptric power, the artifact information being obtained by performing an optical simulation in advance for each dioptric power, under a simulation condition corresponding to an optical condition in an optical system provided in the ophthalmic apparatus for obtaining the image, and calculating a position, a shape, and an intensity of the artifact in the image in advance, the correction circuit is configured to correct the luminance in the correction region, based on the artifact information for each dioptric power, the artifact information includes first artifact information and second artifact information, the first artifact information being information that is shared in common between a plurality of ophthalmic apparatuses having a same model type and same optical system configuration, the second artifact information being information that is specific to the ophthalmic apparatus.

8. An ophthalmic information processing method comprising:

an identifying step of identifying a correction region in an image of a subject's eye, the image being obtained by an ophthalmic apparatus, based on a dioptric power of the subject's eye; and a correction step of correcting a luminance in the correction region identified in the identifying step to remove an artifact of the image, based on a correction amount corresponding to the dioptric power of the subject's eye, wherein the identifying step is performed to identify the correction region based on artifact information for each dioptric power, the artifact information being obtained by performing an optical simulation in advance for each dioptric power, under a simulation condition corresponding to an optical condition in an optical system provided in the ophthalmic apparatus for obtaining the image and calculating a position, a shape, and an intensity of the artifact in the image in advance, the correction step is performed to correct the luminance in the correction region, based on the artifact information for each dioptric power, the artifact information includes first artifact information and second artifact information, the first artifact information being information that is shared in common between a plurality of ophthalmic apparatuses having a same model type and same optical system configuration, the second artifact information being information that is specific to the ophthalmic apparatus.

9. The ophthalmic information processing method of claim 8, further comprising an interpolation step of interpolating artifact information of two or more dioptric powers based on the dioptric power of the subject's eye, the artifact information of two or more dioptric power being identified based on the dioptric power of the subject's eye, wherein the identifying step is performed to identify the correction region based on interpolated artifact information obtained in the interpolation step, and the correction step is performed to correct the luminance in the correction region based on the interpolated artifact information.

10. The ophthalmic information processing method of claim 8, wherein the artifact is a black dot shadow formed by a black dot provided in the ophthalmic apparatus, and the correction step is performed to increase the luminance in the correction region.

11. The ophthalmic information processing method of claim 8, wherein the artifact is a center ghost formed by an objective lens provided in the ophthalmic apparatus, and the correction step is performed to decrease the luminance in the correction region.

12. The ophthalmic information processing method of claim 8, further comprising:

an analysis region identifying step of identifying an analysis region shifted from a reference position in the image by a displacement of the reference position varying in accordance with the dioptric power of the subject's eye, based on the dioptric power of the subject's eye and an optical condition in the optical system of the ophthalmic apparatus; and a correction amount identifying step of identifying the correction amount in the image based on the dioptric power of the subject's eye, wherein the correction step is performed to correct the luminance in the correction region based on the correction amount, the correction region being identified in the analysis region in the identifying step, the analysis region being identified in the analysis region identifying step.

13. The ophthalmic information processing method of claim 8, wherein the ophthalmic apparatus includes a focusing lens that is movable along an optical axis of the optical system, the identifying step is performed to identify the correction region corresponding to the dioptric power of the subject's eye based on a position on the optical axis of the focusing lens, and the correction step is performed to correct the luminance in the correction region based on the position on the optical axis of the focusing lens.

14. A computer readable non-transitory recording medium in which a program for causing a computer to execute each step of an ophthalmic information processing method is recorded, wherein the ophthalmic information processing method comprising:

an identifying step of identifying a correction region in an image of a subject's eye, the image being obtained by an ophthalmic apparatus, based on a dioptric power of the subject's eye; and a correction step of correcting a luminance in the correction region identified in the identifying step to remove an artifact of the image, based on a correction amount corresponding to the dioptric power of the subject's eye, wherein the identifying step is performed to identify the correction region based on artifact information for each dioptric power, the artifact information being obtained by performing an optical simulation in advance for each dioptric power, under a simulation condition corresponding to an optical condition in an optical system provided in the ophthalmic apparatus for obtaining the image, and calculating a position, a shape, and an intensity of the artifact in the image in advance, the correction step is performed to correct the luminance in the correction region, based on the artifact information for each dioptric power, the artifact information includes first artifact information and second artifact information, the first artifact information being information that is shared in common between a plurality of ophthalmic apparatuses having a same model type and same optical system configuration, the second artifact information being information that is specific to the ophthalmic apparatus.

* * * * *